(12) United States Patent
Nguyen et al.

(10) Patent No.: US 6,660,724 B1
(45) Date of Patent: Dec. 9, 2003

(54) COMPOUNDS AND PHARMACEUTICAL COMPOSITIONS CONTAINING THEM

(75) Inventors: Lan Mong Nguyen, Geneva (CH); Eric Niesor, Geneva (CH); Craig Leigh Bentzen, Geneva (CH); Hieu Trung Phan, Geneva (CH); Vinh Van Diep, Geneva (CH); Simon Floret, Geneva (CH); Raymond Azoulay, Geneva (CH); Alexandre Bulla, Geneva (CH); Yves Guyon-Gellin, Geneva (CH); Robert John Ife, Stevenage (GB)

(73) Assignee: Ilex Products, Inc., San Antonio, TX (US)

( * ) Notice: Subject to any disclaimer, the term of this patent is extended or adjusted under 35 U.S.C. 154(b) by 0 days.

(21) Appl. No.: 09/541,217

(22) Filed: Apr. 3, 2000

Related U.S. Application Data

(62) Division of application No. 08/973,669, filed as application No. PCT/EP96/02842 on Jun. 26, 1996, now Pat. No. 6,060,464.

(30) Foreign Application Priority Data

Jun. 30, 1995 (CH) .............................................. 1920/95

(51) Int. Cl.$^7$ ..................... A61K 31/675; C07F 9/58; C07D 213/16; C07D 213/127
(52) U.S. Cl. .......................................... 514/89; 546/22
(58) Field of Search .............................. 514/89; 546/22

(56) References Cited

U.S. PATENT DOCUMENTS 5,424,303 A * 6/1995 Phan et al.

FOREIGN PATENT DOCUMENTS

| EP | 0 559 079 A1 | 2/1993 |
| EP | 0559079 A1 | 9/1993 |
| EP | 0 703 239 A1 | 9/1995 |

OTHER PUBLICATIONS

Chemical Abstracts, vol. 95, No. 17, 1981, Abstract No. 150763b.
J. March, Advanced Organic Chemistry, 1979, Second Edition, pp. 108–111.

* cited by examiner

Primary Examiner—Charanjit S. Aulakh
(74) Attorney, Agent, or Firm—Stephen J. Moloney; Al A. Jecminer

(57) ABSTRACT

Aminophosphonates alpha substituted by phenol groups of formula (I) have lipoprotein(a) lowering activity.

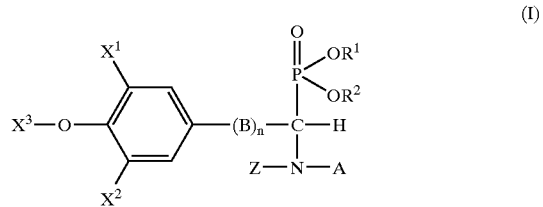

(I)

8 Claims, No Drawings

COMPOUNDS AND PHARMACEUTICAL COMPOSITIONS CONTAINING THEM

This application is a division of Ser. No. 08/973/669 filed Apr. 3, 1998, now U.S. Pat. No. 6,060,464 which is a 371 of International Application No. PCT/EP96/02842 filed Jun. 26, 1996.

This invention relates to a new therapeutic use of aminophosphonate compounds for lowering plasma and tissue levels of lipoprotein(a). In particular, this invention provides a new use of aminophosphonate derivatives, for the preparation of pharmaceutical compositions useful in the treatment of diseases or disorders associated with high plasma and tissue concentrations of lipoprotein(a); such as, for instance artherosclerosis, thrombosis, restenosis after angioplasty and stroke. This invention also provides a method for increasing thrombolysis and preventing thrombosis and a method of treatment of restenosis after angioplasty by administering to a patient in need thereof an aminophosphonate compound at a dose effective for lowering plasma and tissue lipoprotein(a) levels. In addition, this invention also provides a group of new aminophosphonate compounds for use in the above mentioned uses and compositions.

Recent epidemiologic studies have shown a strong association between elevated lipoprotein(a) [Lp(a)] plasma levels and the occurrence of coronary heart disease, stroke and peripheral artery disease. Lp(a) is now recognized as an independent risk factor for cardiovascular diseases; in addition its role in promoting thrombosis by decreasing thrombolysis is increasingly acknowledged, see for instance "Lipoprotein(a) as A Risk Factor for Preclinical Atherosclerosis" P. J. Schreiner, J. D. Morrisett, A. R. Sharrett, W. Patsch, H. A. Tyroler, K. Wu and G. Heiss; Arteriosclerosis and Thrombosis 13 p. 826–833 (1993); "Detection and Quantification of Lipoprotein(a) in the Arterial Wall of 107 Coronary Bypass Patients" M. Rath, A. Niendorf, T. Reblin, M. Dietel, H. J. Krebber and U. Beisiegel; Arteriosclerosis 9, p. 579–592 (1989); and "Lipoprotein(a): Structure, Properties and Possible Involvement in Thrombogenesis and Atherogenesis" A. D. MBewu and P. N. Durrington; Atherosclerosis 85, p. 1–14 (1990). The potential of thrombosis involvement in vessel occlusion and acute cardiovascular syndrome is being increasingly recognized. One of the mechanisms that mediate thrombosis associated with atherosclerotic plaque rupture involves elevated levels of lipoprotein(a). The structure of Lp(a) consists of a low-density lipoprotein (LDL)-like particle with a glycoprotein, apolipoprotein(a) [apo(a)] that is linked via a disulfide bridge to the apo B-100 moiety of the LDL. Structurally there is striking analogy between apo(a) and plasminogen, the precursor of plasmin which cleaves fibrin to dissolve blood clots. However, unlike plasminogen apo(a) is not a substrate for plasminogen activators. This structural resemblance has led researchers to postulate and later demonstrate that apo(a) interferes with the normal physiological function of plasminogen, leading to a potential thrombogenic activity of Lp(a) see for instance:

"Activation of Transforming Growth Factor-β is Inversely Correlated with Three Major Risk Factors for Coronary Artery Disease: Lipoprotein(a), LDL-Cholesterol and Plasminogen Activator Inhibitor-1", A. Chauhan, N. R. Williams, J. C. Metcalfe, A. A. Grace, A. C. Liu, R. M. Lawn, P. R. Kemp, P. M. Schofield and D. J. Grainger; Circulation, Vol 90, No. 4, Part 2, p. I-623 (1994); and "Influence of Human Apo(a) Expression on Fibrinolysis in vivo in Trangenic Mice" T. M. Palabrica, A. C. Liu, M. J. Aronovitz, B. Furie, B. C. Furie and R. Lawn; Circulation, Vol 90, No. 4, Part 2, p. I-623 (1994).

On the basis of its suspected thrombogenic activity, Lp(a) has also been implicated in peripheral artery disease, in particular stroke. Recently clinicians have shown that serum Lp(a) levels were significantly higher in stroke patients than in a reference normal population:

"Lp(a) Lipoprotein in Patients with Acute Stroke" K. Asplund, T. Olsson, M. Viitanen and G. Dahlen; Cerebrovasc. Diseases 1, p. 90–96 (1991).

Restenosis following percutaneous transluminal angioplasty is a common complication occurring in up to 40% of cases within 3–6 months of the intervention. The main cause for restenosis is believed to be abnormal vascular smooth muscle cell activation and proliferation. The proof that high plasma Lp(a) levels are associated with smooth muscle cell proliferation and activation was established in vitro and in vivo by the two following studies:

"Proliferation of Human Smooth Muscle Cells Promoted by Lipoprotein(a)" D. J. Grainger, H. L. Kirschenlohr, J. C. Metcalfe, P. L. Weissberg, D. P. Wade and R. M. Lawn; Science, Vol 260, p.1655–1658 (1993); and "Activation of Transforming Growth Factor-β is Inhibited by Apolipoprotein (a) in vivo", D. J. Grainger, P. R. Kemp, A. C. Liu, R. M. Lawn and J. C. Metcalfe; Circulation, Vol 90, No. 4, Part 2, p. I-623 (1994).

This observation has led to a hypothesis that associates elevated plasma Lp(a) levels with an increased incidence of restenosis. The hypothesis was confirmed by the results of a recent clinical study showing that, in patients with high plasma Lp(a) levels, a reduction of Lp(a) levels by more than 50% by LDL-apheresis significantly reduced the restenosis rate; see for instance:

"Effectiveness of LDL-Apheresis in Preventing Restenosis After Percutaneous Transluminal Coronary Angioplasty (PTCA): LDL-Apheresis Angioplasty Restenosis Trial (L-ART)" H. Yamaguchi, Y. J. Lee, H. Daida, H. Yokoi, H. Miyano, T. Kanoh, S. Ishiwata, K. Kato, H. Nishikawa, F. Takatsu, Y. Kutsumi, H. Mokuno, N. Yamada and A. Noma; Chemistry and Physics of Lipids, Vol 67/68, p. 399–403(1994).

The above discussion has established the rationale for decreasing plasma Lp(a) in patients at risk with elevated levels (>20–30 mg/dl). The Lp(a) concentration in individuals appears to be highly determined by inheritance and is hardly influenced by dietary regimes. Various hormones (i.e. steroid hormones, growth hormones, thyroid hormones) have been shown to regulate plasma levels of Lp(a) in man. Of particular interest, drugs which effectively lower LDL such as the bile acid sequestrant cholestyramine or the HMGCoA reductase inhibitors lovastatin or pravastatin do not affect Lp(a) levels. The drugs of the fibrate family: clofibrate or bezafibrate and the antioxidant drug probucol are equally ineffective. The only drug reported to lower Lp(a) is nicotinic acid. However at the high doses necessary for efficacy (4 g/day) nicotinic acid has several serious side-effects which preclude its wide use: flushing, vasodilation and hepatotoxicity. Therefore the medical need to lower elevated Lp(a) plasma levels, an independent risk factor for cardiovascular disease, is still unmet.

In contrast to LDL, Lp(a) exists only in mammals high in the evolutionary scale (humans and non human primates) and is exclusively synthesized by the liver cells. Cynomolgus monkeys possess Lp(a) that is similar to human Lp(a), including possession of the unique apolipoprotein apo(a). This primate offers an experimental opportunity for studying the synthesis of Lp(a) and the role of Lp(a) in atherosclerosis and thrombosis. Primary cultures of cynomolgus monkey hepatocytes have been selected as the in vitro test for screening aminophosphonate derivatives of formula (I) for their ability to modulate Lp(a) levels. Prior to screening, this assay system had been validated by testing as reference products nicotinic acid and steroid hormones which are known to lower Lp(a) in man.

The present invention relates to the unexpected discovery that aminophosphonate derivatives are effective for lowering plasma and tissue lipoprotein(a). Accordingly, in a first aspect, the present invention provides for the use of a compound of formula (I):

(I)

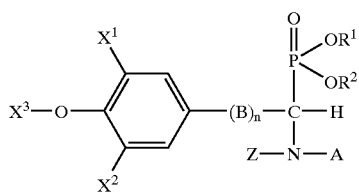

where:

X$^1$, X$^2$, which may be identical or different, are H, a straight or branched alkyl or alkoxy group having from 1 to 8 carbon atoms, a hydroxy group or a nitro group, X$^3$ is H, an alkyl group from 1 to 4 carbon atoms, X$^3$O and one of the two other substituents X$^1$ or X$^2$ may form an alkylidene dioxy ring having from 1 to 4 carbon atoms, R$^1$, R$^2$, identical or different, are H, a straight or branched alkyl group having from 1 to 6 carbon atoms, B is CH$_2$, CH$_2$—CH$_2$ or CH═CH, n is zero or 1, Z is H, a straight or branched alkyl group having from 1 to 8 carbon atoms, an acyl group R$^3$—CO where R$^3$ is an alkyl group from 1 to 4 carbon atoms, a perfluoroalkyl group from 1 to 4 carbon atoms, A is H, CH$_2$—CH═CH$_2$, a straight, branched or cyclic alkyl group having from 1 to 8 carbon atoms, or is selected from the following groups:

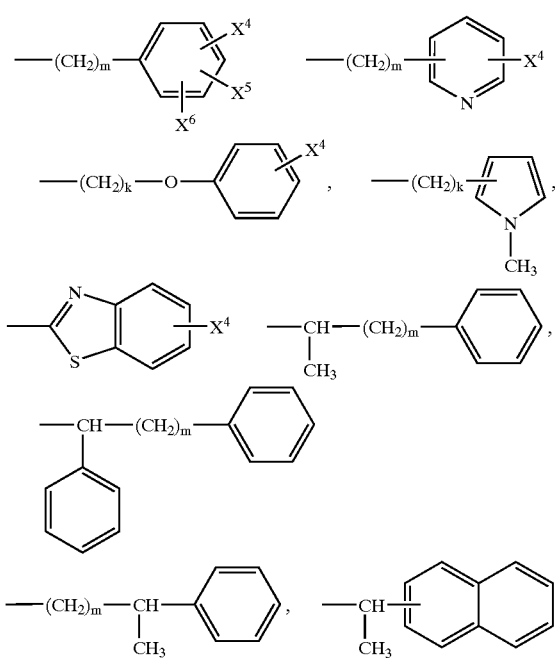

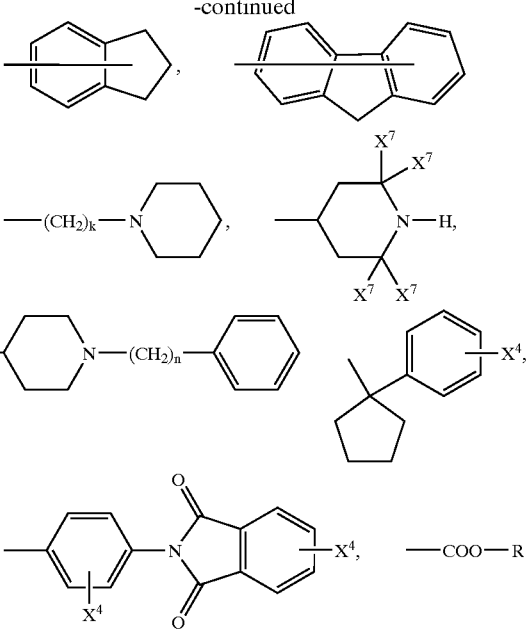

where k is an integer from 2 to 4, m is 0 or an integer from 1 to 5, X$^4$, X$^5$, X$^6$, identical or different, are H, a straight or branched alkyl or alkoxy group from 1 to 8 carbon atoms, a hydroxy, trifluoromethyl, nitro, amino, dimethylamino, diethylamino group, a halogen atom (F, Cl, Br, I), X$^4$ and X$^5$ may form an alkylidendioxy ring having from 1 to 4 carbon atoms, X$^7$ is H or CH$_3$, R is a straight or branched alkyl group having from 1 to 6 carbon atoms, an aryl or arylalkyl group from 6 to 9 carbon atoms;

or a pharmaceutically acceptable salt thereof;

in the manufacture of a medicament for lowering plasma and tissue lipoprotein(a).

European Patent Application EP 0'559'079A (1993) [corresponding to the U.S. Pat. No. 5,424,303] discloses compounds of formula (I) as well as their use in decreasing plasma cholesterol and blood peroxides.

Preferred compounds of formula (I) for use in the manufacture of a medicament for lowering plasma and tissue lipoprotein(a) are those of the formula (Ia):

(Ia)

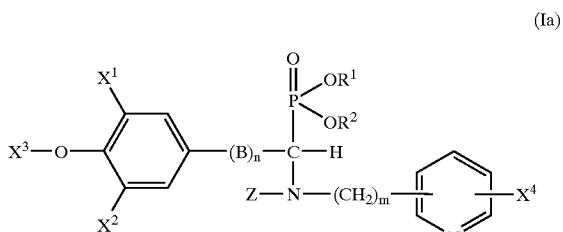

where B, R$^1$, R$^2$, X$^1$, X$^2$, X$^3$, X$^4$, Z, n and m are as hereinbefore defined;

or a pharmaceutically acceptable salt thereof.

Certain compounds within the scope of formula (Ia) are novel and are particularly useful in lowering plasma and tissue lipoprotein(a).

Accordingly, in a further aspect, this invention provides aminophosphonate derivatives of formula (Ia) where:

X$^1$ is H, C$_{(1-8)}$alkyl or C$_{(1-8)}$alkoxy;

X$^2$ is C$_{(1-8)}$alkyl or C$_{(1-8)}$alkoxy;

$X^3$ is H, $C_{(1-4)}$alkyl, or $X^3O$ and one of the two other substituents $X^1$ or $X^2$ may form an alkylidene dioxy ring having from 1 to 4 carbon atoms;

$R^1$, $R^2$, which may be identical or different, are H or $C_{(1-6)}$alkyl;

B is $CH_2$—$CH_2$, $CH$=$CH$ or $CH_2$;

n is zero or 1;

Z is H or $C_{(1-8)}$alkyl;

m is an integer from 0 to 5;

$X^4$ is H, $C_{(1-8)}$alkyl, $C_{(1-8)}$alkoxy, or halo;

and the pyridyl ring is attached by the ring carbon α- or β- to the nitrogen (2- or 3-pyridyl);

or a salt, preferably a pharmaceutically acceptable salt, thereof; and excluding:

Diethyl α-(3,5-di-tert-butyl-4-hydroxyphenyl)-N-(3-pyridyl)aminomethylphosphonate;

Diethyl α-(3,5-di-tert-butyl-4-hydroxyphenyl)-N-(2-picolyl)aminomethylphosphonate;

Diethyl α-(3,5-di-tert-butyl-4-hydroxyphenyl)-N-(3-picolyl)aminomethylphosphonate;

Diethyl α-(3,5-di-tert-butyl-4-hydroxyphenyl)-N-methyl-N-(3-picolyl)aminomethylphosphonate;

Diethyl α-(3,5-di-tert-butyl-4-hydroxyphenyl)-N-(2-pyridylethyl)aminomethylphosphonate, and Diethyl α-(3,5-di-tert-butyl-4-hydroxyphenyl)-N-(4-picolyl)aminomethylphosphonate.

Suitably, $X^1$ is H, $C_{(1-4)}$alkyl or $C_{(1-4)}$alkoxy, preferably $C_{(1-3)}$alkyl or $C_{(1-3)}$alkoxy, more preferably hydrogen, methyl or methoxy.

Suitably, $X^2$ is $C_{(1-4)}$alkyl or $C_{(1-4)}$alkoxy, preferably $C_{(1-3)}$alkyl or $C_{(1-3)}$alkoxy, more preferably methyl or methoxy.

Suitably, $X^1$ and $X^2$ are both alkoxy or one of $X^1$ and $X^2$ is alkyl and the other is alkoxy, or one of $X^1$ and $X^2$ is $C_{(1-4)}$alkyl and the other of $X^1$ and $X^2$ is $C_{(1-3)}$alkyl.

Suitable combinations of $X^1$ and $X^2$ include methoxy and methoxy, methoxy and methyl, n-propyl or isobutyl, methyl and methyl or t-butyl, respectively.

Preferably, $X^3$ is hydrogen.

Preferably, $(B)_n$ is a direct bond.

Preferably, $R^1$ and $R^2$ is each a $C_{(1-3)}$alkyl group, more preferably, a $C_2$ or $C_3$ alkyl group, in particular $R^1$ and $R^2$ is ethyl or isopropyl.

Preferably, Z is hydrogen.

Preferably, $X^4$ is hydrogen or methyl which is preferably on the ring carbon adjacent to N.

Preferably, the pyridyl ring is attached by the ring carbon β- to the nitrogen (3-pyridyl).

When used herein, the terms 'alkyl' and 'alkoxy' include both straight and branched groups, for instance, methyl, ethyl, n-propyl, iso-propyl, n-butyl, iso-butyl, s-butyl, t-butyl, etc.

Preferred compounds of formula (Ia) include:

Diisopropyl α-(4-hydroxy-3-methoxy-5-methylphenyl)-N-(3-pyridyl)-aminomethylphosphonate;

Diisopropyl α-(3,5-dimethoxy-4-hydroxyphenyl)-N-(3-pyridyl)-aminomethylphosphonate;

Diethyl α-(3-methyl-4-hydroxy-5-t-butylphenyl)-N-(3-pyridyl)-aminomethylphosphonate;

Diethyl α-(3,5-dimethoxy-4-hydroxyphenyl)-N-(3-pyridyl)-aminomethylphosphonate; and Diethyl α-(3,5dimethyl-4-hydroxyphenyl)-N-(3pyridyl)-aminomethylphosphonate.

Independently from the previously published activity, the present invention relates to the unexpected discovery that aminophosphonate derivatives of formula (I) are effective for decreasing Lp(a) production by primary cultures of Cynomolgus monkey hepatocytes. Lp(a) of these primates is similar in immunologic properties to human Lp(a) and occurs in an almost identical frequency distribution of plasma concentrations, see for instance:

"Plasma Lipoprotein(a) Concentration is Controlled by Apolipoprotein(a) Protein Size and the Abundance of Hepatic Apo(a) mRNA in a Cynomolgus Monkey Model", N. Azrolan, D. Gavish and J. Breslow; J. Biol. Chem., Vol 266, p. 13866–13872 (1991).

Therefore the compounds of this invention are potentially useful for decreasing Lp(a) in man and thus provide a therapeutic benefit.

In particular, this invention provides a new therapeutic use for aminophosphonate compounds of formula (I) as Lp(a) lowering agents. Diseases associated with elevated plasma and tissue levels of lipoprotein(a) include, for instance, coronary heart disease, peripheral artery disease, intermittent claudication, thrombosis, restenosis after angioplasty, extracranial carotid atherosclerosis, stroke and atherosclerosis occuring after heart transplant.

The recently discovered Lp(a) lowering activity of the aminophosphonates of formula (I) is independent from their previously reported pharmacological activities of decreasing plasma cholesterol and blood peroxides. Recent clinical studies have shown that neither the hypocholesterolemic drug pravastatin nor the antioxidant drug probucol can decrease Lp(a) levels in man. See for example:

"Serum Lp(a) Concentrations are Unaffected by Treatment with the HMG-CoA Reductase Inhibitor Pravastatin: Results of a 2-Year Investigation" H. G. Fieseler, V. W. Armstrong, E. Wieland, J. Thiery, E. Schiltz, A. K. Walli and D. Seidel; Clinica Chimica Acta, Vol 204, p. 291–300 (1991); and "Lack of Effect of Probucol on Serum Lipoprotein(a) Levels", A. Noma; Atherosclerosis 79, p. 267–269 (1989).

For therapeutic use the compounds of the present invention will generally be administered in a standard pharmaceutical composition obtained by admixture with a pharmaceutical carrier selected with regard to the intended route of administration and standard pharmaceutical practice. For example, they may be administered orally in the form of tablets containing such excipients as starch or lactose, or in capsule, ovules or lozenges either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic with blood. The choice of form for administration as well as effective dosages will vary depending, inter alia, on the condition being treated. The choice of mode administration and dosage is within the skill of the art.

The compounds of structure (I) and their pharmaceutically acceptable salts which are active when given orally can be formulated as liquids, for example syrups, suspensions or emulsions or as solids for example, tablets, capsules and lozenges. A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavouring or colouring agents.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

A typical suppository formulation comprises a compound of structure (I) or a pharmaceutically acceptable salt thereof which is active when administered in this way, with a binding and/or lubricating agent such as polymeric glycols, gelatins or cocoa butter or other low melting vegetable or synthetic waxes or fats.

Preferably the composition is in unit dose form such as a tablet or capsule.

Each dosage unit for oral administration contains preferably from 1 to 250 mg (and for parenteral administration contains preferably from 0.1 to 25 mg) of a compound of the structure (I) or a pharmaceutically acceptable salt thereof calculated as the free base.

The pharmaceutically acceptable compounds of the invention will normally be administered to a subject in a daily dosage regimen. For an adult patient this may be, for example, an oral dose of between 1 mg and 500 mg, preferably between 1 mg and 250 mg, or an intravenous, subcutaneous, or intramuscular dose of between 0.1 mg and 100 mg, preferably between 0.1 mg and 25 mg, of the compound of the structure (I) or a pharmaceutically acceptable salt thereof calculated as the free base, the compound being administered 1 to 4 times per day.

Compounds of formula (I) may be prepared according to the processes described in European Patent Application EP 0 559 079-A (1993[corresponding to the U.S. Pat. No. 5,424,303]. This process which has two variants is shown in the following general scheme:

GENERAL SYNTHESIS SCHEME

Variant 1

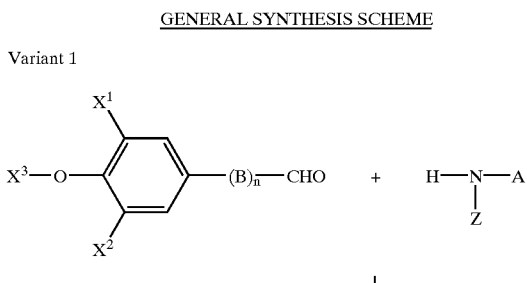

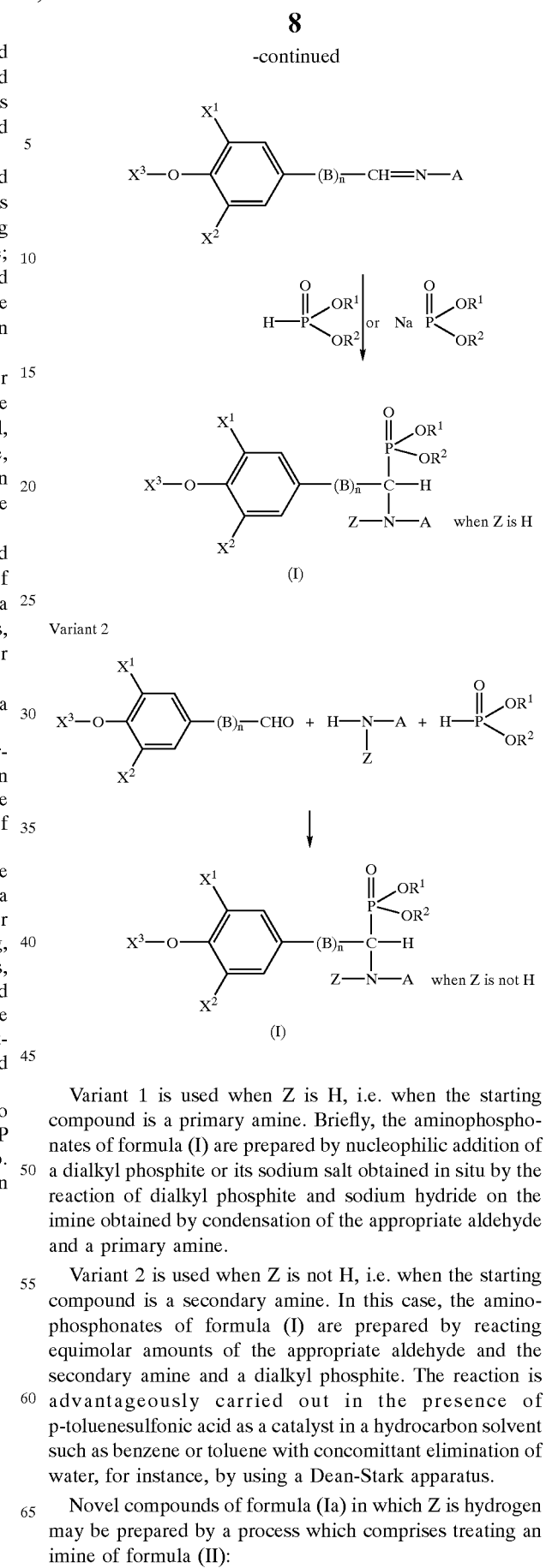

Variant 1 is used when Z is H, i.e. when the starting compound is a primary amine. Briefly, the aminophosphonates of formula (I) are prepared by nucleophilic addition of a dialkyl phosphite or its sodium salt obtained in situ by the reaction of dialkyl phosphite and sodium hydride on the imine obtained by condensation of the appropriate aldehyde and a primary amine.

Variant 2 is used when Z is not H, i.e. when the starting compound is a secondary amine. In this case, the aminophosphonates of formula (I) are prepared by reacting equimolar amounts of the appropriate aldehyde and the secondary amine and a dialkyl phosphite. The reaction is advantageously carried out in the presence of p-toluenesulfonic acid as a catalyst in a hydrocarbon solvent such as benzene or toluene with concomittant elimination of water, for instance, by using a Dean-Stark apparatus.

Novel compounds of formula (Ia) in which Z is hydrogen may be prepared by a process which comprises treating an imine of formula (II):

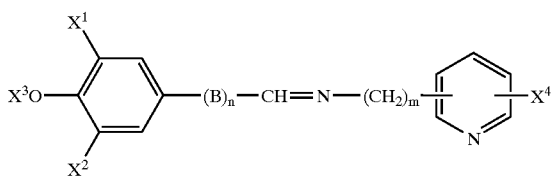

(II)

in which B, $X^1$, $X^2$, $X^3$, $X^4$, m and n are as hereinbefore defined;
with a phosphite compound of formula (III):

$HPO(OR^1)(OR^2)$ (III)

in which $R^1$ and $R^2$ are as hereinbefore defined; or a trialkyl silyl derivative thereof, preferably the trimethyl silyl phosphite, or a metal salt thereof, for instance the sodium salt, formed in situ by treatment of the compound of formula (III) with a suitable base, for instance sodium hydride, ethoxide or methoxide.

The reaction may be carried out in the presence or absence of a catalyst. Suitable catalysts include amine such as diethylamine or triethylamine. The reaction may be carried out in the absence or presence of a solvent. Suitable solvents include petroleum ether, benzene, toluene, diethyl ether, tetrahydrofuran, 1,2-dimethoxyethane. Suitable reaction temperatures are in the range 30 to 140° C.

The imine compound of formula (II) may be obtained by condensing an aldehyde compound of formula (V):

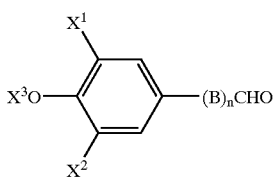

(V)

in which B, $X^1$, $X^2$, $X^3$ and n are as hereinbefore defined;
with a primary amine of formula (VI):

$H_2NA$ (VI)

in which A is as hereinbefore defined;
under imine forming conditions.

Suitably, the condensation may be effected with or without a catalyst in a solvent such as ether, tetrahydrofuran, benzene, toluene or ethanol. Suitable catalysts include molecular sieve, an acid such as glacial acetic acid, p-toluene sulphonic acid, thionyl chloride, titanium tetrachloride, boron trifluoride etherate, or a base such as potassium carbonate. The reaction is suitably carried out at a temperature in the range 0° C. to the boiling point of the solvent being used. For less reactive amines/aldehydes, the reaction may be usefully carried out in a Dean-Stark apparatus.

Novel compounds of formula (Ia) in which Z is not hydrogen may be prepared by a process which comprises treating equimolar amounts of an aldehyde of formula (V), a secondary amine of formula (VII):

HNZA (VII)

in which Z is a $C_{(1-8)}$alkyl group and A is as hereinbefore defined; and a phosphite of formula (III), suitably in the presence of p-toluenesulfonic acid as a catalyst, in a hydrocarbon solvent such as petroleum ether, benzene, toluene or xylene, at a temperature between ambient temperature and the boiling point of the solvent being used, and with concomittant elimination of water, for instance, by using a Dean-Stark apparatus.

Compounds of formula (Ia) in which m is not zero may also be prepared by a process which comprises treating a compound of formula (VIII):

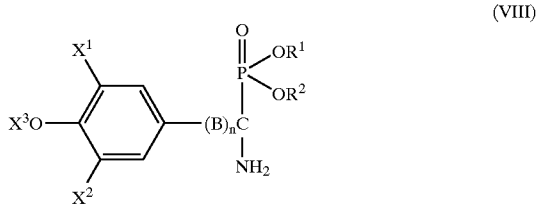

(VIII)

in which B, $R^1$, $R^2$, $X^1$, $X^2$, $X^3$ and n are as hereinbefore defined;
an aldehyde of formula (IX):

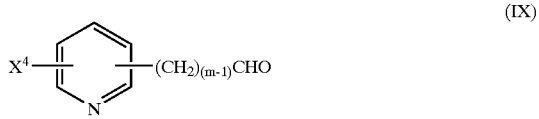

(IX)

in which m is an integer from 1 to 5 and $X^4$ is as hereinbefore defined;
under reductive amination conditions.

Suitable such conditions include carrying out the reaction in the presence of sodium cyanoborohydride in an alcoholic solvent, preferably methanol, at a pH between 3 to 6 and at a temperature between 0° C. and 25° C.

A compound of formula (VIII) may be obtained according to the process hereinbefore described for a compound of formula (Ia) from an aldehyde of formula (V), a secondary amine of formula (VII) in which Z is protecting group which can be removed by hydrogenolysis, for instance an α substituted benzyl or bezyloxycarbonyl and a phosphite of formula (III). This forms an intermediate which is then subjected to hydrogenolysis according to standard conditions, to give a compound of formula (VIII).

Through their amino function, the aminophosphonate ester (I) can form salts of inorganic acids such as HCl, $H_2SO_4$ or with organic acids such as oxalic acid, maleic acid, sulfonic acids, etc. An example of hydrochloride salt of aminophosphonate (I) is provided (example 5). All these salts are integral part of this invention.

Compounds of structure (I) are racemates as they have at least one chiral center which is the carbon atom in position alpha to the phosphonate group. The compounds (I) therefore exist in the two enantiomeric forms. The racemic mixtures (50% of each enantiomer) and the pure enantiomers are comprised in the scope of this application. In certain cases, it may be desirable to separate the enantiomers.

In a further aspect, the present invention provides a process for the enantiomeric synthesis of a derivative of formula (I) which process comprises treating either of the (+) or (−) enantiomer of the α-substituted aminomethylphosphonate of formula (X):

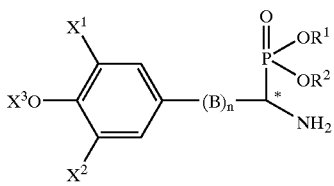

(X)

in which B, $R^1$, $R^2$, $X^1$, $X^2$, $X^3$ and n are as hereinbefore defined;

with an aldehyde of formula (XI):

$R^3$—CHO (XI)

in which $R^3$ is as hereinbefore defined;
under reductive amination conditions.

Suitable such conditions include carrying out the reaction in the presence of sodium cyanoborohydride in an alcoholic solvent, preferably methanol, at a pH between 3 to 6 and at a temperature between 0° C. and 25° C.

The key α-substituted primary aminomethylphosphonate of formula (X) is obtained by treating an aldehyde of formula (V), as hereinbefore defined, with (+) or (−)α-methylbenzylamine to form an intermediate imine which is then reacted with a phosphite ester $HPO(OR^1)(OR^2)$ to give a mixture of diastereoisomers which may be separated by conventional techniques, for instance fractional crystallisation or chromatography. Hydrogenolysis can then be used to remove the benzyl group from nitrogen, to give the α-substituted primary aminomethyl-phosphonate of formula (X). This approach is illustrated by the preparation of enantiomers of compounds No. 7 and 15 of Table 1. Alternately. the resolution of the aminophosphonate racemates can be effected by preparative chiral chromatography, in particular chiral HPLC. The experimental conditions for chromatographic separation of enantiomers of compound No. 20 are provided. With either separation method, final enantiomeric purity can be ascertained by measuring the specific rotations of the separated isomers.

The structure of compounds of formula (I) were established by their elemental analysis, their infrared (IR), mass (MS) and nuclear magnetic resonance (NMR) spectra The purity of the compounds was checked by thin layer, gas liquid or high performance liquid chromatographies.

The invention is further described in the following examples which are intended to illustrate the invention without limiting its scope. In the tables, n is normal, i is iso, s is secondary and t is tertiary. In the description of the NMR spectra, respectively s is singlet, d doublet, t triplet and m multiplet TsOH is p-toluenesulfonic acid monohydrate. The temperatures were recorded in degrees Celsius and the melting points are not corrected. In the measurement of optical activity, an enantiomer which rotates the plane of polarized light to the right is called dextrorotatory and is designated (+) or (D). Conversely, levorotatory defines an enantiomer which rotates the plane of polarized light to the left, designated (−) or (L). Unless otherwise indicated, the physical constants and biological data given for aminophosphonates of formula (I) refer to racemates.

EXAMPLE 1

Dimethyl α-(3,5-di-tert-Butyl-4-hydroxyphenyl)-N-(3-pyridyl)-amino-methylphosphonate

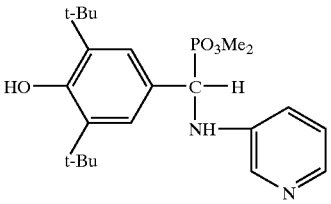

A mixture of 50 g (0.206 mol) of 3,5-di-tert-butyl-4-hydroxybenzaldehyde and 20.3 g (2.16 mol) of 3-aminopyridine dissolved in 300 ml toluene and a catalytic amount of p-toluenesulfonic acid (ca. 50 mg) contained in a flask, connected to a Dean Stark apparatus was refluxed for 17 h. The solution was evaporated to dryness to give a solid which was purified by recrystallisation from ligroin: mp=125–130°, IR (KBr): 1590 cm$^{-1}$: CH═N.

Dimethyl phosphite (63.8 g, 0.58 mol) was added to 60 g (0.19 mol) of the previously described imine dissolved in 230 ml THF and the mixture was refluxed for 6 h. The solvent was evaporated and the residue was purified by column chromatography (SiO$_2$, 9/1 CHCl$_3$/MeOH). Recrystallisation from a mixture of methyl-tert-butyl ether/petroleum ether gave a white solid, mp=168–170° C.

IR (KBr)=3300 cm$^{-1}$: NH, 1240: P═O, 1030: P—O—C; NMR (CDCl$_3$): δ=8.06, 7.96, 7.4 and 6.9 (4m, 1H each): aromatic H, 3-pyridyl, 7.2 (d, $J_{P-H}$=2 Hz, 2H): aromatic H, substituted phenyl, 5.24 (s, 1H): OH, 4.66 (d, $J_{P-H}$=22 Hz, 1H): CH—PO$_3$Me$_2$, 4.75–4.68 (m, 1H): NH, 3.74 and 3.39=(two d, J=11 Hz): P—O—CH$_3$, 1.42 (s, 18H): tert-Bu; MS: m/e=419: M$^+$–1,311 (100%): M$^+$ —PO$_3$Me$_2$.

EXAMPLE 2

Diethyl α-(3,5-di-tert-Butyl-4-hydroxyphenyl)-N-(2-pyridyl)-amino-methylphosphonate

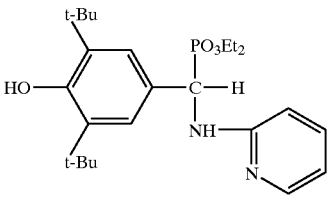

The process described in example 1 was employed using 2-aminopyridine as the amine and diethyl phosphite as the phosphonate reagent. The title compound was purified by column chromatography (95/5 CHCl$_3$/MeOH) to yield a solid (61%); mp=116–118° (AcOEt-ligroin).

MS (m/e)=448: M$^+$, 311: M$^+$ —PO$_3$Et$_2$, 78 (100%): C$_5$H$_4$N; δ=8.09, 7.38 and 6.57 and 6.44 (4m, 1H each): aromatic H, 2-pyridyl, 7.28 (d, $J_{P-H}$=2 Hz, 2H): aromatic H, substituted phenyl, 5.46 (dd, J=9 and 22 Hz, 1H): CH—PO$_3$Et$_2$, 5.3 (m, 1H): N—H, 4.14–3.66 (3m, 4H total): P—O—CH$_2$—CH3, 1.42 (s, 18H): tert-Bu, 1.21 and 1.16 (2 t, 3H each): P—O—CH$_2$—CH$_3$.

EXAMPLE 3

Diethyl α-(3,5-di-tert-Butyl-4-hydroxyphenyl)-N-[5-(2-chloropyridyl)]-aminomethylphosphonate

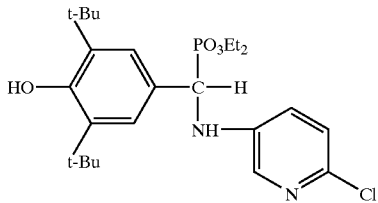

The process described in example 1 was employed using 5-amino-2-chloropyridine as the amine and diethyl phosphite as the phosphonate reagent. The title compound was obtained in 50% yield after column chromatography (98/2 CHCl$_3$/MeOH) and trituration in petroleum ether, mp=124–126° C.

MS (m/e)=483: M$^+$+1,345 (100%), 347 (30%): M$^+$—PO$_3$Et$_2$: NMR (CDCl$_3$): δ=7.78, 7.05 and 6.09 (3H): aromatic H, 3-pyridyl, 7.18 (d, J=2 Hz, 2H): aromatic H, substituted phenyl, 5.22 (s, 1H): OH, 4.83 (t, J=8 Hz): N—H, 4.57 (dd, J=7.5 and 22.5 Hz): C$\underline{H}$—PO$_3$—Et$_2$, 4.1, 3.86 and 3.56 (3m, 4H): P—O—C$\underline{H}_2$—CH$_3$, 1.40 (s, 18H): t-Bu, 1.28 and 1.05 (2t, J=7 Hz): P—O—CH$_2$—C$\underline{H}_3$.

EXAMPLE 4

Diethyl α-(3,5-di-tert-Butyl-4-hydroxyphenyl)-N-acetyl-N-(4-picolyl)-aminomethylphosphonate

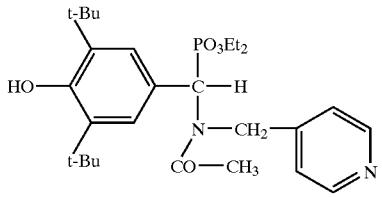

A mixture of acetic anhydride (1.4 g, 14 mmol), diethyl α-(3,5-di-tert-butyl-4-hydroxyphenyl)-N-(4-picolyl)-aminomethylphosphonate (6 g, 13 mmol) and triethyl amine (1.9 ml, 14 mmol) in 20 ml toluene was refluxed for 16 h. The reaction mixture was extracted with brine, dried and evaporated to dryness. The residue was recrystallized in a mixture of dichloromethane and petroleum ether to give 3.7 g (57% yield); mp=160–162° C.

MS (m/e): 504: M$^+$, 461: M$^+$ —COCH$_3$, 367: M$^+$ —PO$_3$—Et$_2$, 325 (100%): M$^+$ +1-PO$_3$Et$_2$—COCH$_3$.

EXAMPLE 5

Hydrochloride Salt of Diethyl α-(3,5-di-tert-Butyl-4-hydroxyphenyl)-N-(3-pyridyl) aminomethylphosphonate

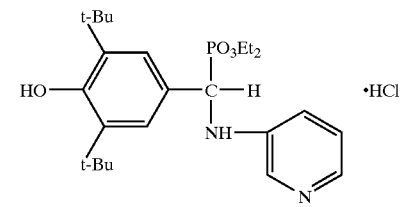

Diethyl α-(3,5-di-tert-butyl-4-hydroxyphenyl)-N-(3-pyridyl) aminomethylphosphonate (3 g, 6.7 mmol) was dissolved with slight warming in 60 ml toluene and the resulting solution was saturated with gaseous hydrogen chloride. After 16 h at 0° C. the mixture was evaporated to dryness and the residue was recrystallized in EtOH; mp=193–194° C.

| | | | | | |
|---|---|---|---|---|---|
| % Calc. | C 59.43 | H 7.90 | Cl 7.31 | N 5.78 | P 6.39 |
| % Found | C 59.53 | H 8.10 | Cl 7.02 | N 5.72 | P 6.21 |

EXAMPLE 6

Diethyl α-(3,4-Methylenedioxy-N-(3-pyridyl)-aminomethylphosphonate

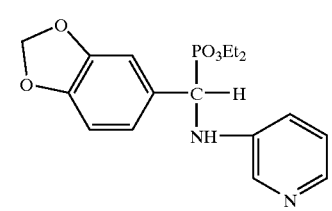

The process described in example 8 was followed. The title compound was purified by column chromatography (9/1 CHCl$_3$/MeOH); 60% yield, mp=98–99° C., C$_{17}$H$_{21}$N$_2$O$_5$P.

IR (KBr)=1240 cm$^{-1}$: P=O, 1030: P—O—C; MS (m/e)= 365 M$^+$ +1, 227 (100%): M$^+$ —PO$_3$Et$_2$; NMR (CDCl$_3$) δ=8.1, 7.95, 7.05 and 6.95 (4m, 1H each): aromatic H, 3-pyridyl, 6.90, 6.85, 6.75 (3m, 3H): aromatic H, substituted phenyl, 5.95 (2H): =O—C$\underline{H}_2$—O, 4.86 (d×d, 1H, J=8 and 10 Hz): N—H, 4.63 (d×d, 1H, J=8 and 24 Hz): C$\underline{H}$—PO$_3$Et$_2$, 4.18–3.70 (3m, 4H total): P—O—C$\underline{H}_2$—CH$_3$, 1.31 and 1.16: (2t, J=7 Hz): P—O—CH$_2$—C$\underline{H}_3$.

EXAMPLE 7

Diethyl α-(4-Hydroxyphenyl)-N-(3-pyridyl)-aminomethylphosphonate

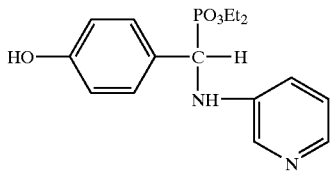

4-Hydroxybenzaldehyde (6 g, 49 mmol) was reacted at room temperature with 3-aminopyridine (4.5 g, 52 mmol) in 30 ml THF at room temperature to give 9.9 g of a light brown solid. The imine so obtained (5.9 g, 30 mmol) was dissolved in 50 ml THF, diethyl phosphite was added in two portions, one at the beginning of the reaction and the other after 6 h at reflux, (total amount: 8.2 g, 60 mmol). The reaction mixture was refluxed overnight. Filtration of the precipitate formed gave 7.5 g (75%) of a tan solid, mp=210–212° C. (EtOH).

MS (m/e)=337: M$^+$ +1, 199 (100%): M$^+$ —PO$_3$Et$_2$; NMR (DMSO-d6): δ=9.35 (s, 1H); OH, 8.15, 7.7, 7.1 and 7.0 (4m, 1H each): aromatic H, 3-pyridyl, 6.5 (dxd, 1H): N—H, 7.3 and 6.7 (2m, 2H each): aromatic H, 4-hydroxyphenyl, 4.93 (dxd, 1H): C$\underline{H}$—PO$_3$Et$_2$, 4.1–3.6 (3m, 4H total): P—O—C$\underline{H}_2$—CH$_3$, 1.15 and 1.02 (2t, 3H each): P—O—CH$_2$—C$\underline{H}_3$.

EXAMPLE 8

Diethyl α-(3,5-Dimethoxy-4-hydroxyphenyl)-N-(3-pyridyl)amino-methylphosphonate

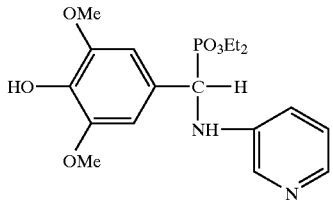

A mixture of 3 g (16.4 mmol) of syringaldehyde and 1.63 g (17.3 mmol) of 3-aminopyridine dissolved in 10 ml toluene and a catalytic amount of p-toluenesulfonic acid (ca. 5 mg) contained in a flask connected to a Dean Stark apparatus was refluxed for 17 h. The solution was evaporated to dryness to give 4.2 g (100%) of the crude imine. Diethyl phosphite (4.8 g, 35 mmol) was added to 4.2 g (17.3 mmol) of the previously described imine dissolved in 10 ml THF and the mixture was refluxed for 7 h. Another amount of diethyl phosphite (4.8 g, 35 mmol) was added and the mixture was refluxed overnight (total reaction time: 17 h). The solvent and the excess of diethyl phosphite were evaporated and the residue was recrystallized from a mixture of ethanol and dichloromethane to give 4.2 g (61%) of a white solid, mp=181–183°.

IR (KBr)=1240 cm$^{-1}$: P═O and 1030: P—O—C; MS (m/e)=397: M$^+$ +1,259 (100%): M$^+$ —PO$_3$Et$_2$; NMR (CDCl$_3$): δ=8.08, 7.98, 7.04 and 6.84 (4m, 1H each): aromatic H, 3-pyridyl, 6.69 (d, J=2 Hz, 2H): aromatic H, substituted phenyl, 5.8 (broad, 1H): O$\underline{H}$, 4.84 (dxd, 1H, J=7 and 10 Hz): N—H, 4.62 (dxd, 1H, J=7 and 23 Hz): C$\underline{H}$—PO$_3$Et$_2$, 4.18–3.65 (3m, 4H total): P—O—C$\underline{H}_2$—CH$_3$, 3.86 (s, 6H): OC$\underline{H}_3$, 1.31 and 1.16: (2t, J=7 Hz): P—O—CH$_2$—C$\underline{H}_3$.

| Elemental analysis: C$_{18}$H$_{25}$N$_2$O$_6$P | | | | |
|---|---|---|---|---|
| % Calc. | C 54.54 | H 6.36 | N 7.07 | P 7.81 |
| % Found | C 54.50 | H 6.38 | N 6.99 | P 7.65 |

EXAMPLE 9

Diethyl α-(3,4,5-Trimethoxyphenyl)-N-(3-pyridyl)-aminomethylphosphonate

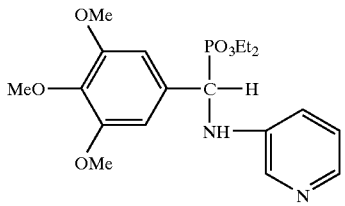

A mixture of 3,4,5-trimethoxybenzaldehyde (10 g, 51 mmol) and 3-aminopyridine (4.8 g, 51 mmol) and a catalytic amount of TsOH in 50 ml toluene was refluxed for 16 h in a flask connected to a Dean-Stark trap. Evaporation of toluene gave 12.9 g (93%) of the crude imine which was used directly in the next reaction. A 50 ml THF mixture containing the imine (6g, 22 mmol) and diethyl phosphite (6.1 g introduced at the beginning and 6.1 g after 4 h, total amount=12.2 g, 88 mmol) was refluxed for 8 h. The residue after evaporation of THF and excess of HPO$_3$Et$_2$ was triturated in petroleum ether to give 7.12 g (79%) of a white solid, mp=135–137° C.

MS (m/e)=410: M$^+$, 273 (100%): M$^+$ —PO$_3$Et$_2$; NMR (CDCl$_3$): δ=8.1, 8.0, 7.05 and 6.85 (4m, 1H each): aromatic H, 3-pyridyl, 6.69 and 6.68: (d, J=2 Hz, 2H): aromatic H, substituted phenyl, 4.86 (dxd, 1H, J=8 and 10 Hz): N—H, 4.63 (dxd, 1H, J=7 and 23 Hz): C$\underline{H}$—PO$_3$Et$_2$, 4.18–3.70 (3m, 4H total): P—O—C$\underline{H}_2$—CH$_3$, 3.86 (two s, 9H): OC$\underline{H}_3$, 1.31 and 1.16: (2t, J=7 Hz): P—O—CH$_2$—C$\underline{H}_3$.

EXAMPLE 10

Diethyl α-(3-Ethoxy-4-hydroxyphenyl)-N-(3-pyridyl)-aminomethylphosphonate

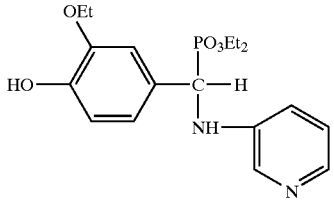

A 50 ml toluene solution containing 3-ethoxy-4-hydroxybenzaldehyde (10 g, 60 mmol), 3-aminopyridine (5.6 g, 60 mmol) and 50 mg of TsOH placed in a flask connected to a Dean-Stark trap was refluxed for 4 h to give 14.62 g (95%) of the corresponding imine.

To a suspension of sodium hydride (1.19 g of a 60% mixture, 30 mmol) in 20 ml dry THF was added HPO$_3$Et$_2$ (9.12 g 66 mmol) under nitrogen and the resulting mixture was stirred until the initial turbid suspension became completely clear. To this solution of NaPO₃Et₂ was added the above imine (8 g, 33 mmol) dissolved in 10 ml THF and the resulting solution was refluxed for 2 h. THF was evaporated and the residue was partitioned into H₂O and CH₂Cl₂. Evaporation of the dried organic phase gave 3.1 g of a white solid, mp=184–187° C.

MS: (m/e)=380: M⁺, 243: M⁺ —PO₃Et₂; NMR (DMSO-d6): δ=8.9 (s, 1H): OH, 8.15, 7.3, 7.0 and 6.9 (1H each): aromatic H, 3-pyridyl, 7.1 (m, 2H) and 6.68 (d, J=8 Hz, 1H): aromatic H, phenyl, 6.5 (dxd, J=6 and 10 Hz): NH, 4.92 (dxd, J=10 and 24 Hz): C$\underline{H}$—PO₃Et₂, 4.05–3.6 (4m, 6H total): P—O—C$\underline{H}_2$—CH₃ and OC$\underline{H}_2$ CH₃, 1.29 (t, J=7 Hz, 3H): O—CH₂—C$\underline{H}_3$, 1.16 and 1.04 (2t, J=7 Hz, 3H each): P—O—CH₂—C$\underline{H}_3$.

EXAMPLE 11

Diethyl α-(4-Hydroxy-3-methoxyphenyl)-N-(3-pyridyl)-aminomethylphosphonate

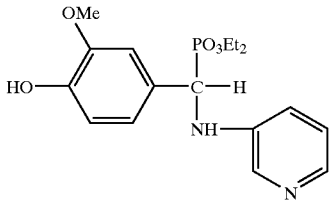

The procedure described in example 10 was followed, using 4-hydroxy-3-methoxybenzaldehyde as the starting material. The title compound is a white solid, mp=170–173° C.

MS (m/e)=366: M⁺, 229: M⁺ —PO₃Et₂; NMR (DMSO-d6) δ=8.9 (s, 1H): OH, 8.15, 7.75, 7.0 and 6.9 (4m, 4H): aromatic H, 3-pyridyl, 7.1 (m, 2H) and 6.7 (d, J=8 Hz, 1H): aromatic H, phenyl, 6.5 (dxd, J=6 and 10 Hz): NH, 4.92 (dxd, J=10 and 24 Hz): C$\underline{H}$—PO₃Et₂, 4.05–3.6 (3m, 4 H total): P—O—C$\underline{H}_2$—CH₃, 3.72 (s, 3H): OCH₃, 1.17 and 1.4 (2t, J=7 Hz, 6H): P—O—CH₃—C$\underline{H}_3$.

EXAMPLE 12

Diethyl α-(3,5-Dimethoxy-4hydroxyphenyl)-N-(4-picolyl)-aminomethylphosphonate

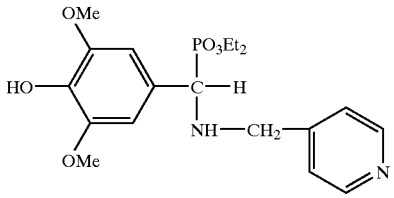

A solution of 2.5 g (13.7 mmol) syringaldehyde and 1.6 g (14.4 mmol) 4-picolylamine dissolved in 100 ml toluene contained in a flask connected to a Dean-Stark apparatus was refluxed for 3 h. Toluene was evaporated under vacuum then the residue dissolved in 10 ml THF was heated with 5.1 g (36.8 mmol) diethyl phosphite for 6 h. THF was evaporated and the residue was purified by column chromatography (SiO₂, 95/5 CHCl₃/MeOH). Recrystallisation in a mixture of CH₂Cl₂-petroleum ether gave 3.7 g (45%) of a solid, mp=124–126° C.

MS (m/e)=410: M⁺, 273: M⁺ —PO₃Et₂; NMR (CDCl₃) δ=8.55 and 7.22 (2m, 4H): aromatic H, 4-picolyl, 6.75 (d, J=2 Hz, 2H): aromatic H, phenyl, 4.15–3.77 (several m, 5 H): P—O—C$\underline{H}_2$—CH₃ and C$\underline{H}$—PO₃Et₂, 3.89 (s, 6H): OCH₃, 3.82 and 3.62 (2d, J=14 Hz): NH—C$\underline{H}_2$—Py, 1.33 and 1.16 (2t, J=7 Hz, 6H): P—O—CH₂—C$\underline{H}_3$.

EXAMPLE 13

Diethyl α-(3,5-Dimethoxy-4-hydroxyphenyl)-N-(3-picolyl)-aminomethylphosphonate

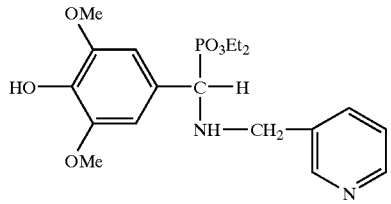

The procedure described in example 12 was followed, using 3-picolylamine as the starting material. The title compound was purified by column chromatography (9/1 CHCl₃/MeOH) to give a thick yellow oil. Recrystallization from CH₂Cl₂-Petroleum ether gave a tan solid, mp=99–101°.

MS (m/e): 410: M⁺, 273 =M⁺ —PO₃Et2; NMR (CDCl₃) δ=8.51, 8.50, 7.64 and 7.25 (4m, 4H): aromatic H, 3-picolyl, 6.65 (d, J=2 Hz, 2H): aromatic H, phenyl, 7.75 (broad, 1H): OH, 4.15–3.75 (several m, 5H): P—O—C$\underline{H}_2$—CH₃ and C$\underline{H}$—PO₃Et₂, 3.9 (s, 6H): OCH₃, 3.82 and 3.61 (2d, J=14 Hz, 2H): NH—C$\underline{H}_2$—Py, 1.31 and 1.16 (2t, J=7 Hz, 6H): P—O—CH₂—C$\underline{H}_3$.

EXAMPLE 14

Diethyl α-(3,5-Dimethoxy-4-hydroxyphenyl)-N-(2-pyridyl)-amino-methylphosphonate

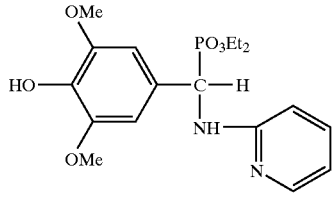

A mixture of 3.64 g (20 mmol) of syringaldehyde and 1.88 g (20 mmol) of 2-aminopyridine dissolved in 20 ml toluene and a catalytic amount of TsOH contained in a flask connected to a Dean Stark apparatus was refluxed for 24 h. The solution was evaporated to dryness to give 5.2 g (100%) of the crude imine. Diethyl phosphite (5.8 g, 42 mmol) was added to 3.6 g (14 mmol) of the previously described imine dissolved in 25 ml THF and the mixture was refluxed for 20 h. The solvent and the excess of diethyl phosphite were evaporated and the residue was recrystallized from ethanol to give 4.2 g (76%) of a white solid. mp=163–165° C.

IR (KBr)=1240 cm⁻¹: P=O and 1030: P—O—C; MS (m/e)=397: M⁺ +1, 259 (100%): M⁺ —PO₃Et₂; NMR (CDCl₃): δ=8.08, 7.37, 6.60 and 6.41 (4m, 1H each): aromatic H, 2-pyridyl, 6.76 (d, J=2 Hz, 2H): aromatic H, substituted phenyl, 5.6 (s, 1H): O$\underline{H}$, 5.39 (m, 1H): N—H, 5.37 (dxd, 1H, J=9 and 28 Hz): C$\underline{H}$—PO₃Et₂, 4.18–3.69

(3m, 4H total): P—O—CH$_2$—CH$_3$, 3.87 (s, 6H): OCH$_3$, 1.24 and 1.15: (2t, J=7 Hz): P—O—CH$_2$—CH$_3$.

EXAMPLE 15

Diethyl α-(3,5-Dimethoxy-4-hydroxyphenyl)-N-(4-pyridyl)-aminomethyl Phosphonate

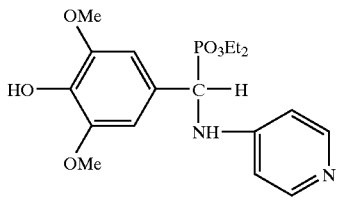

A 25 ml toluene solution containing syringaldehyde (3.64 g, 20 mmol), 4 aminopyridine (1.9 g, 20 mmol) and 5 mg of TsOH placed in a flask connected to a Dean-Stark trap was refluxed for 48 h to give 5.0 g (95%) of the corresponding imine.

To a suspension of sodium hydride (0.87 g of a 60% mixture, 20 mmol) in 25 ml dry THF was added HPO$_3$Et$_2$ (4.14 g, 30 mmol) under nitrogen and the resulting mixture was stirred until the initial turbid suspension became completely clear. To this solution of NaPO$_3$Et$_2$ was added the above imine (2.6 g, 10 mmol) dissolved in 5 ml THF and the resulting solution was refluxed for 2 h. THF was evaporated and the residue was partitioned into H$_2$O and CH$_2$Cl$_2$. Evaporation of the dried organic phase gave a white solid which was recrystallized in EtOH (1.84 g, 45%); mp=172–174° C.

MS (m/e)=396: M$^+$, 259 (100%): M$^+$ —PO$_3$Et$_2$; NMR (CDCl$_3$): δ=8.18, 8.16, 6.48 and 6.46 (4m, 1H each): aromatic H, 4-pyridyl, 6.67 (d, J=2 Hz, 2H): aromatic H, substituted phenyl, 5.27 (dxd, 1H, J=7 and 10 Hz): N—H, 4.66 (dxd, 1H, J=7 and 23 Hz): CH—PO$_3$Et$_2$, 4.18-3.60 (3m, 4H total): P—O—CH$_2$—CH$_3$, 3.87 (s, 6H): OCH$_3$, 1.30 and 1.15: (2t, J=7 Hz): P—O—CH$_2$—CH$_3$.

EXAMPLE 16

Enantiomers of Diethyl α-(3,5-di-tert-Butyl-4-hydroxyphenyl)-N-(4-picoyl)-aminomethylphosphonate

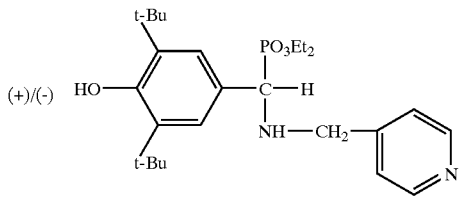

a) 3,5-Di-tert-butyl-4-hydroxybenzaldehyde (30 g, 123.5 mmol) and (R)-(+)-1-phenyl-ethylamine (15.7 g, 129.7 mmol) were stirred in 100 ml of THF at room temperature for one day. The solution was dried on MgSO$_4$ and concentrated. The corresponding imine was recrystallized from ligroin (38 g; 88% yield; mp=127–128° C.).

The imine (30 g, 89 mmol) and diethylphosphite (15.4 g, 111.3 mmol) were refluxed in 80 ml of toluene for 5 hours. The mixture was evaporated to dryness. HPLC assay of the residue showed that one of the diastereomers is formed predominantly (84% vs 3% of the reaction mixture). The major diastereomer of diethyl α-(3,5-di-tert-butyl-4-hydroxyphenyl)-N-(1-phenyl-ethyl)-aminomethylphosphonate was isolated by successive crystallizations (10 g); [α]$_D^{27}$+8.33° (c=1.649, CHCl$_3$); mp=105–106° C.). (+)-Diethyl α-(3,5-di-tert-butyl-4-hydroxyphenyl)-N-(1-phenyl-ethyl)-aminomethylphosphonate (9.5 g, 20 mmol) was hydrogenated in ethanol in the presence of 2.5 g of 10% Pd on charcoal to give (–)-diethyl α-(3,5-di-tert-butyl-4-hydroxyphenyl)-aminomethylphosphonate (5.6 g; 76% yield; mp=143–145° C. (recrystalized from ligroin/CH$_2$Cl$_2$); [α]$_D^{22}$–12.12° (c=1.650, CHCl$_3$).

(–)-Diethyl α-(3,5-di-tert-butyl-4-hydroxyphenyl)-aminomethylphosphonate (11 g, 29.6 mmol) and pyridine 4carboxaldehyde (6.3 g, 59.3 mmol) were dissolved in 125 ml of MeOH. The mixture was acidified with concentrated HCl (blue bromophenol indicator). After half an hour of stirring at room temperature, NaBH$_3$CN (5.6 g, 89 mmol) dissolved in 30 ml MeOH was added and the pH was adjusted again with HCl. The reaction mixture was stirred at room temperature for 4 hours then evaporated to dryness and extracted with CH$_2$Cl$_2$ and water. The organic phase was dried over MgSO$_4$ and evaporated. The residue was separated by column chromatography (silicagel, 95/5 CHCl$_3$/MeOH to give (–)-diethyl α-(3,5-di-tert-butyl-4-hydroxyphenyl)-N-(4-picolyl)-aminomethylphosphonate [(11 g; 80% yield; mp=66–69° C.; [α]$_D^{21}$–44.05° (c=1.992, CHCl$_3$)].

b) 3,5-Di-tert-butyl-4-hydroxybenzaldehyde (30 g, 123.5 mmol) and (S)-(–)-1-phenyl-ethylamine (15.7 g, 129.7 mmol) were stirred in 100 ml of THF for one day to give the corresponding imine (36.5 g; 88% yield; mp=127–128° C.).

The imine (20 g, 59.3 mmol) and diethylphosphite (10.2 g, 74.2 mmol) were refluxed in 60 ml of toluene for 7 hours. The mixture was evaporated to dryness. HPLC assay of the residue indicated the diastereomeric ratio to be 60 to 40% in addition to starting materials. The latter were stripped off by column chromatography on silicagel (98/2 CH$_2$Cl$_2$/MeOH). The fractions containing the mixture of diastereomers were evaporated to dryness and recrystallized three times from ligroin/MTBE to yield the major diastereomer of diethyl α-(3,5-di-tert-butyl-4-hydroxyphenyl)-N-(1-phenyl-ethyl)-aminomethylphosphonate) [12 g; mp=104–105° C.; [α]$_D^{28}$–10.53° (c=1.643, CHCl$_3$)].

(–)-Diethyl α-(3,5-di-tert-butyl-4-hydroxyphenyl)-N-(1-phenyl-ethyl)-aminomethylphosphonate (42 g, 88.4 mmol) was hydrogenated in ethanol in the presence of 6 g of 10% Pd on charcoal to give (+)-diethyl α-(3,5-di-tert-butyl-4-hydroxyphenyl)-aminomethylphosphonate (24.5 g; 75% yield; mp=143–144° C. (recrystallized from ligroin/MTBE); [α]$_D^{29}$+11.04° (c=1.714, CHCl$_3$)].

(+)-Diethyl α-(3,5-di-tert-butyl-4-hydroxyphenyl)-aminomethylphosphonate (11 g, 29.6 mmol) and pyridine-4-carboxaldehyde (6.35 g, 59.3 mmol) in 125 ml of MeOH were reacted with NaBH$_3$CN (5.6 g, 89 mmol) in the same manner as described for the (–) enantiomer. Column chromatography on silicagel (95/5 CHCl$_3$/MeOH) gave (+)diethyl α-(3,5-di-tert-butyl-4-hydroxyphenyl)-N-(4-picolyl)-aminomethylphosphonate (12 g, 87% yield; mp=67–70° C.; [α]$_D^{21}$+43.03° (c=1.984, CHCl$_3$)].

EXAMPLE 17

Enantiomers of Diethyl α-(3,5-di-tert-Butyl-4-hydroxyphenyl)-N-(3-picolyl)-aminomethylphosphonate

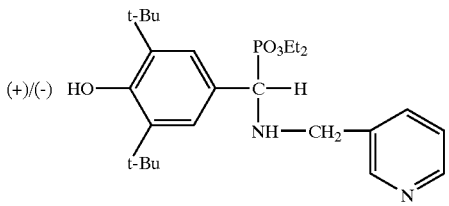

a) In the same manner as described in example 16, (+)-diethyl α-(3,5-di-tert-butyl-4-hydroxyphenyl) aminomethylphosphonate (1 g, 2.7 mmol) and pyridine-3-carboxaldehyde (0.43 g, 4 mmol) were reacted with NaBH$_3$CN (0.34 g, 5.4 mmol) in MeOH for 5 hours at room temperature to yield after trituration in petroleum ether (+)-diethyl-α-(3,5-di-tert-butyl-4-hydroxyphenyl)-N-(3-picolyl)-aminomethylphosphonate (1 g, 80% yield; mp=116–119° C.; $[\alpha]_D^{23}$+42.88° (c=1.614, CHCl$_3$)].

b) Respectively, (−)-diethyl-α-(3,5-di-tert-butyl-4-hydroxyphenyl)-aminomethylphosphonate (1 g, 2.7 mmol) and pyridine-3-carboxaldehyde (0.43 g, 4 mmol) were reacted with NaBH$_3$CN (0.34 g, 5.4 mmol) in MeOH to give (−)-diethyl-α-(3,5-di-tert-butyl-4-hydroxyphenyl)-N-(3-picolyl)aminomethylphosphonate (0.7 g, 56%; mp=118–120° C.).

EXAMPLE 18

Enantiomers of Diethyl α-(3,5-Dimethoxy-4-hydroxyphenyl)-N-(3-pyridyl)-aminomethylphosphonate

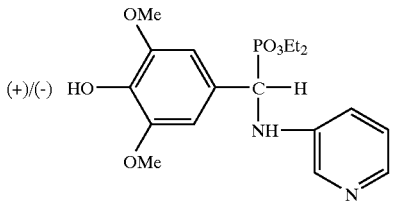

The enantiomers of a racemic mixture were separated by preparative HPLC on Chiralcel OD and isocratic elution with hexane/ethanol (9:1), UV detection at 254 run. Baseline separation was achieved, and the contents of both peaks were evaporated to white solids in which none of the other isomer could be detected by analytical HPLC.

First peak: retention time 18 min, $[\alpha]_D^{20}$−7.4° (c=0.244% w/v, EtOH); Second peak: retention time 34 min, $[\alpha]_D^{20}$+8.3° (c=0.255% w/V, EtOH).

The structures of both enantiomers were confirmed by NMR and MS spectroscopies and elemental analysis.

| Elemental analysis: C$_{18}$H$_{25}$N$_2$O$_6$P | | | |
|---|---|---|---|
| % Calc. (+) Enantiomer: | C 54.54 | H 6.36 | N 7.07 |
| mp: 153–157° % Found (−) Enantiomer: | C 53.85 | H 6.22 | N 6.81 |
| mp: 155–158° % Found | C 54.25 | H 6.24 | N 6.94 |

EXAMPLE 19

Enantiomers of Diethyl α-(3,5-di-tert-Butyl-4-hydroxyphenyl)-N-(3-phenylpropyl)aminomethylphosphonate

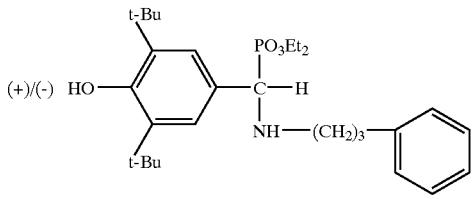

a) (−)-Diethyl-α-(3,5-di-tert-butyl-4-hydroxyphenyl)-aminomethylphosphonate (1.7 g, 4.5 mmol) and 3-phenylpropionaldehyde (0.6 g, 4.5 mmol) in 20 ml of absolute methanol were stirred under nitrogen, at room temperature for 30 min. NaBH$_3$CN (0.3 g, 4.5 mmol) dissolved in 10 ml of methanol was added and the mixture was allowed to react at room temperature for another hour. The reaction mixture was evaporated to dryness and the residue dissolved in CH$_2$Cl$_2$. The organic phase was washed with water, then dried over MgSO$_4$. Column chromatography with 98/2 CHCl$_3$/MeOH as eluent gave (−)-diethyl-α-(3,5-di-tert-butyl-4-hydroxyphenyl)-N-(3-phenylpropyl) aminomethylphosphonate [1.2 g; 56% yield; $[\alpha]_D^{25}$+33.1° (c=2.055, CHCl$_3$)].

b) (+) Diethyl α-(3,5-di-tert-butyl-4-hydroxyphenyl)-aminomethylphosphonate (1.2 g, 3.2 mmol) and 3-phenylpropionaldehyde (0.4 g, 3.2 mmol) in 20 ml of absolute methanol were reacted in the same manner with NaBH$_3$CN (0.2 g, 3.2 mmol) in 10 ml of methanol to yield after column chromatography, (+) diethyl α-(3,5-di-tert-butyl-4-hydroxyphenyl)-N-(3-phenylpropyl)-aminomethylphosphonate [0.94 g; 61% yield; $[\alpha]_D^{25}$+31.1° (c=1.930, CHCl$_3$)].

c)—The structures of both enantiomers were confirmed by IR, NMR and MS. They were separated by analytical HPLC on Chiralpak AD and isocratic elution with hexane/2-propanol (9:1/v:v).

EXAMPLE 20

Diisopropyl α-(3,5-Dimethoxy-4-hydroxyphenyl)-N-(3-pyridyl-aminomethylphosphonate

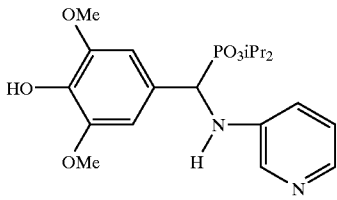

Diisopropyl phosphite (3.3 g, 20 mmol) was added to 2.58 g (10 mmol) of 3,5-dimethoxy-4-hydroxybenzaldehyde N-(3-pyridyl) imine dissolved in 15 ml toluene and the mixture was refluxed for 17 h. The solvent and the excess of diisopropyl phosphite were evaporated and the residue was purified by column chromatography (9/1 CH$_2$Cl$_2$/MeOH) and recrystallisation from a mixture of EtOH/AcOEt to give 1.56 g (37%) of a white solid, mp=157–160°.

MS (m/e)=424: M$^+$, 259 (100%): M$^+$ —PO$_3$iPr$_2$; NMR (CDCl$_3$): δ=8.08. 7.96, 7.03 and 6.84 (4m, 1H each): aromatic H, 3-pyridyl, 6.69 (d, J=2 Hz, 2H): aromatic H, substituted phenyl, 5.8 (broad, 1H): OH, 4.82 (dxd, 1H, J=7 and 10 Hz): N—H, 4.55 (dxd, 1H, J=7 and 23 Hz): CH—PO$_3$iPr$_2$, 4.75–4.65 and 4.55–4.45 (2m, 2H total): P—O—CH—(CH$_3$)$_2$, 3.86 (s, 6H): OCH$_3$, 1.34, 1.28, 1.24 and 0.9: (4d, J=7 Hz): P—O—CH—(CH$_3$)$_2$.

EXAMPLE 21

Diisopropyl α-(4-Hydroxy-3-methoxy-5-methylphenyl)-N-(3-pyridyl)-amino-methylphosphonate

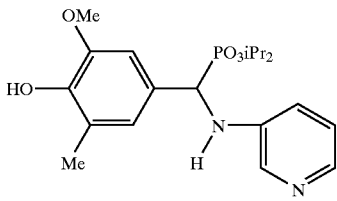

A mixture of 1.9 g (11 mmol) of 4-hydroxy-3-methoxy-5-methylbenzaldehyde (mp=98–100°) and 1.08 g (11 mmol) of 3-aminopyridine dissolved in 15 ml toluene and a catalytic amount of p-toluenesulfonic acid (ca. 5 mg) contained in a flask connected to a Dean Stark apparatus was refluxed for 15 h. The solution was evaporated to dryness to give 2.7 g (100%) of the crude imine.

Diisopropyl phosphite (5.48 g, 33 mmol) was added to 2.77 g (11 mmol) of the above imine dissolved in 20 ml THF and the mixture was refluxed for 24 h. The solvent and the excess of diisopropyl phosphite were evaporated and the residue was purified by column chromatography (95/5 CHCl$_3$/MeOH) and recrystallisation from a mixture of petroleum ether/CH$_2$Cl$_2$ to yield 1.9 g (43%) of a white solid, mp=123–124°.

MS (m/e)=408: M$^+$, 243 (100%): M$^+$ —PO$_3$iPr$_2$ NMR (CDCl$_3$): δ=8.07, 7.95, 7.02 and 6.84 (4m, 1H each): aromatic H, 3-pyridyl, 6.83–6.81: (m, 2H): aromatic H, substituted phenyl, 5.8 (s, 1H): OH, 4.78 (dxd, 1H, J=7.5 and 10 Hz): N—H, 4.30 (dxd, 1H, J=7.5 and 23 Hz): CH—PO$_3$iPr$_2$, 4.73–4.65 and 4.48–4.40 (2m, 2H total): P—O—CH—(CH$_3$)$_2$, 3.85 (s, 3H): OCH$_3$, 2.22 (s, 3H): CH$_3$, 1.33, 1.26, 1.24 and 0.96: (4d, J=7 Hz): P—O—CH—(CH$_3$)$_2$.

EXAMPLE 22

Diisopropyl α-(3-n-Butyl-4-hydroxy-5-methoxyphenyl)-N-(3-pyridyl)-amino-methylphosphonate

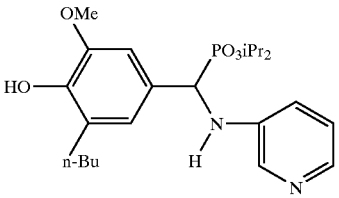

A mixture of 6.1 g (30 mmol) of 3-n-butyl-4-hydroxy-5-methoxybenzaldehyde and 2.76 g (30 mmol) of 3-aminopyridine dissolved in 50 ml toluene and a catalytic amount of p-toluenesulfonic acid (ca. 5 mg) contained in a flask connected to a Dean Stark apparatus was refluxed for 16 h. The solution was evaporated to dryness to give 7.8 g (94%) of the crude imine.

Diisopropyl phosphite (4.20 g, 25 mmol) was added to 2.4 g (8 mmol) of the above imine dissolved in 30 ml THF and the mixture was refluxed for 24 h. The solvent and the excess of diisopropyl phosphite were evaporated and the residue was purified by column chromatography (95/5 CHCl$_3$/MeOH) and recrystallisation from a mixture of petroleum ether/CH$_2$Cl$_2$ to yield 1.9 g (43%) of a white solid, mp=142–144°.

MS (m/e)=450: M$^+$, 285 (100%): M$^+$ —PO$_3$iPr$_2$; NMR (CDCl$_3$): δ=8.07, 7.95, 7.0 and 6.84 (4m, 1H each): aromatic H, 3-pyridyl, 6.83–6.80: (m, 2H): aromatic H, substituted phenyl, 5.8 (s, 1H): OH, 4.74 (dxd, 1H, J=7.5 and 10 Hz): N—H, 4.54 (dxd, 1H, J=7.5 and 23 Hz): CH—PO$_3$iPr$_2$, 4.75–4.65 and 4.50–4.40 (2m, 2H total): P—O—CH—(CH$_3$)$_2$, 3.85 (s, 3H): OCH$_3$, 2.60 (t, 2H), 1.5 (m, 2H), 1.31 (m, 2H) and 0.90 (t, 3H): n-Bu, 1.33, 1.26, 1.24 and 0.94: (4d, J=7 Hz): P—O—CH—(CH$_3$)$_2$.

EXAMPLE 23

Diethyl α-(3,5-Dimethoxy-4-hydroxyphenyl)-N-methyl-N-(3-picolyl)aminomethylphosphonate

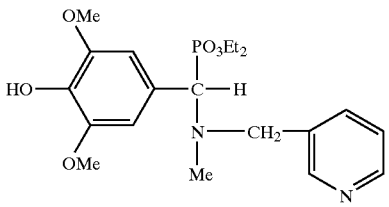

A mixture of 3.0 g (16.5 mmol) of syringaldehyde, 2.03 g (16.6 mmol) of N-methyl-3-picolylamine and 2.3g (16.6 mmol) diethyl phosphite dissolved in 15 ml toluene and a catalytic amount of p-toluenesulfonic acid (ca. 5 mg) contained in a flask connected to a Dean Stark apparatus was refluxed for 2 h. The solution was evaporated and the residue was purified by column chromatography (95/5 CHCl$_3$/MeOH) to yield 3.2 g (46%) of a yellow oil.

MS (m/e)=287: M⁺ —PO₃Et₂; NMR (CDCl₃): δ=8.55, 8.51, 7.72 and 7.27 (4m, 1H each): aromatic H, 3-picolyl, 6.73 (d, 2H): aromatic H, substituted phenyl, 5.8 (broad, 1H): O$\underline{H}$, 4.25, 3.94 and 3.7 (3m, 4H): P—O—C$\underline{H}_2$—CH₃, 3.89 (d, J=23 Hz, 1H): C$\underline{H}$—PO₃Et₂, 3.9 and 3.4 (2d, 2H): N(CH₃)—C$\underline{H}_2$—Py, 3.91 (s, 6H): OC$\underline{H}_3$, 2.41 (s, 3H): N(C$\underline{H}_3$)—CH₂—Py, 1.39 and 1.08 (2t, J=7 Hz, 6 H): P—O—CH₂C$\underline{H}_3$.

EXAMPLE 24

Diisopropyl α-(4-Hydroxy-3-methoxy-5-methylphenyl)-N-methyl-N-(3-picolyl)-aminomethylphosphonate

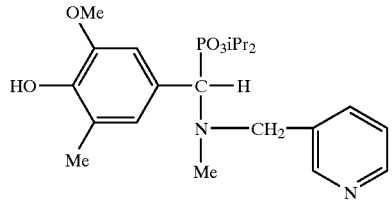

A mixture of 2.0 g (12 mmol) of 4-hydroxy-3-methoxy-5-methylbenzaldehyde, 1.8 g (13.2 mmol) of N-methyl-3-picolylamine and 2.2 g (13.2 mmol) diisopropyl phosphite dissolved in 15 ml toluene and a catalytic amount of p-toluenesulfonic acid (ca. 2 mg) contained in a flask connected to a Dean Stark apparatus was refluxed for 2 h. The solution was evaporated and the residue was purified by column chromatography (95/5 CHCl₃/MeOH) to yield 2.1 g (40%) of a yellow oil.

MS (m/e)=271 (100%): M⁺ —PO₃iPr₂; NMR (CDCl₃): δ=8.54, 8.50, 7.72 and 7.24 (4m, 1H each): aromatic H, 3-picolyl, 6.97 and 6.77 (2 m, 2H): aromatic H. substituted phenyl, 5.75 (broad, 1H): O$\underline{H}$, 4.86–4.78 and 4.51–4.42 (2m, 2H total): P—O$\underline{H}$—(CH₃)₂, 3.84 (d, J=24 Hz, 1H): C$\underline{H}$—PO₃iPr₂, 3.97 and 3.34 (2d, J=13,5 Hz, 2H): N(CH₃)—C$\underline{H}_2$—Py, 3.91 (s, 3H): OC$\underline{H}_3$, 2.36 (s, 3H): C$\underline{H}_3$, 2.26 (s, 3H): N(C$\underline{H}_3$)—CH₂—Py, 1.39, 1.37, 1.21 and 0.83 (4d, J=7 Hz, 12H): P—O—CH(C$\underline{H}_3$)₂.

The following compounds may also be obtained in an analogous manner to Examples 1 to 24:

Diethyl α-(4-hydroxy-3-methoxy-5-n-propylphenyl)-N-(3-pyridyl)-aminomethylphosphonate;

Diisopropyl α-(4-hydroxy-3-methoxy-5-n-propylphenyl)-N-(3-pyridyl)-aminomethylphosphonate;

Diethyl α-(3-i-butyl-4-hydroxy-5-methoxyphenyl)-N-(3-pyridyl)-aminomethylphosphonate; and Diisopropyl α-(3-i-butyl-4-hydroxy-5-methoxyphenyl)-N-(3-pyridyl)-aminomethylphosphonate.

Table 1 lists the physicochemical data of compounds of formula (I) that were prepared by the methods illustrated by examples 1–24 of this application. These methods are disclosed in EP 0 559 079A (corresponding to the U.S. Pat. No. 5,424,303).

TABLE 1

Aminophosphonates of formula (I)

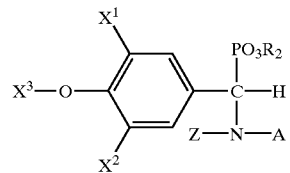

(I)

| Cpd | X¹ | X² | X³ | Z | A | R | mp (° C.) | Microanalysis |
|---|---|---|---|---|---|---|---|---|
| 1 | tBu | tBu | H | H | 3-pyridyl | Me | 168–170 | C₂₂H₃₃N₂O₄P |
| 2 | tBu | tBu | H | H | 3-pyridyl | Et | 155–156 | C₂₄H₃₇N₂O₄P |
| 3 | tBu | tBu | H | H | 3-pyridyl | iPr | 135–137 | C₂₆H₄₁N₂O₄P |
| 4 | tBu | tBu | H | H | 3-pyridyl | nPr | 133–135 | C₂₆H₄₁N₂O₄P |
| 5 | tBu | tBu | H | H | 3-pyridyl | nBu | 112–114 | C₂₈H₄₅N₂O₄P |
| 6 | tBu | tBu | H | H | 4-picolyl | Me | 120–122 | C₂₃H₃₅N₂O₄P |
| 7 | tBu | tBu | H | H | 4-picolyl | Et | 87–91 | C₂₅H₃₉N₂O₄P |
| 8 | tBu | tBu | H | H | 4-picolyl | iPr | 126–128 | C₂₇H₄₃N₂O₄P |
| 9 | tBu | tBu | H | H | 4-picolyl | nPr | 108–110 | C₂₇H₄₃N₂O₄P |
| 10 | tBu | tBu | H | H | 4-picolyl | nBu | 60–61 | C₂₉H₄₇N₂O₄P |
| 11 | tBu | tBu | H | COMe | 4-picolyl | Et | 160–162 | C₂₇H₄₁N₂O₅P |
| 12 | tBu | tBu | H | H | 5-(2-chloropyridyl) | Et | 124–126 | C₂₄H₃₆ClN₂O₄P |
| 13 | tBu | tBu | H | H | 2-pyridyl | Et | 116–118 | C₂₄H₃₇N₂O₄P |
| 14 | tBu | tBu | H | H | 4-pyridyl | Et | 116–119 | C₂₄H₃₇N₂O₄P |
| 15 | tBu | tBu | H | H | 3-picolyl | Et | 100–101 | C₂₅H₃₉N₂O₄P |
| 16 | tBu | tBu | H | H | 2-picolyl | Et | 90–91 | C₂₅H₃₉N₂O₄P |
| 17 | tBu | tBu | H | H | 2-(2-pyridyl)ethyl | Et | 76–78 | C₂₆H₄₁N₂O₄P |
| 18 | H | H | H | H | 3-pyridyl | Et | 210–212 | C₁₆H₂₁N₂O₄P |
| 19 | OMe | OMe | H | H | 3-pyridyl | Me | 186–187 | C₁₆H₂₁N₂O₆P |
| 20 | OMe | OMe | H | H | 3-pyridyl | Et | 181–183 | C₁₈H₂₅N₂O₆P |
| 21 | OMe | OMe | H | H | 3-pyridyl | iPr | 157–160 | C₂₀H₂₉N₂O₆P |
| 22 | OMe | OMe | H | H | 2-picolyl | Et | oil | C₁₉H₂₇N₂O₆P |
| 23 | OMe | OMe | H | H | 3-picolyl | Et | 99–101 | C₁₉H₂₇N₂O₆P |
| 24 | OMe | OMe | H | H | 4-picolyl | Et | 125–127 | C₁₉H₂₇N₂O₆P |
| 25 | OMe | H | H | H | 3-pyridyl | Et | 171–173 | C₁₇H₂₃N₂O₅P |
| 26 | OEt | H | H | H | 3-pyridyl | Et | 185–187 | C₁₈H₂₅N₂O₅P |

TABLE 1-continued

| | $X^1$ | $X^2$ | $X^3$ | $X^4$ | A | R | mp (° C.) | Microanalysis |
|---|---|---|---|---|---|---|---|---|
| 27 | OMe | OMe | Me | H | 3-pyridyl | Et | 134–136 | $C_{19}H_{27}N_2O_6P$ |
| 28 | Me | Me | H | H | 3-pyridyl | Et | 176–178 | $C_{18}H_{25}N_2O_4P$ |
| 29 | OMe | OMe | H | H | 2-pyridyl | Et | 163–165 | $C_{18}H_{25}N_2O_6P$ |
| 30 | OMe | OMe | H | H | 4-pyridyl | Et | 172–174 | $C_{18}H_{25}N_2O_6P$ |
| 31 | OMe | OMe | H | H | 3-pyridyl | nPr | 142–143 | $C_{20}H_{29}N_2O_6P$ |
| 32 | OMe | OMe | H | H | 3-pyridyl | nBu | 158–160 | $C_{22}H_{33}N_2O_6P$ |
| 33 | OMe | $NO_2$ | H | H | 3-pyridyl | Et | 212–213 | $C_{17}H_{22}N_3O_7P$ |
| 34 | OMe | OMe | H | H | 5-(2-chloropyridyl) | Et | 193–195 | $C_{18}H_{24}ClN_2O_6P$ |
| 35 | OMe | OMe | H | H | 5-(2-methoxypyridyl) | Et | 135–137 | $C_{19}H_{27}N_2O_7P$ |
| 36 | OMe | OMe | H | H | 3-(2-methylpyridyl) | iPr | 148–150 | $C_{21}H_{31}N_2O_6P$ |
| 37 | OMe | OMe | H | H | 5-(2-methylpyridyl) | Et | 189–190 | $C_{19}H_{27}N_2O_6P$ |
| 38 | OMe | OMe | H | H | 5-(2-methylpyridyl) | iPr | 150–152 | $C_{21}H_{31}N_2O_6P$ |
| 39 | Me | t-Bu | H | H | 3-pyridyl | Et | 90–91 | $C_{21}H_{31}N_2O_4P$ |
| 40 | iPr | iPr | H | H | 3-pyridyl | Et | 174–176 | $C_{22}H_{33}N_2O_4P$ |
| 41 | sBu | sBu | H | H | 3-pyridyl | Et | 140–141 | $C_{24}H_{37}N_2O_4P$ |
| 42 | Et | Et | H | H | 3-pyridyl | Et | 170–171 | $C_{20}H_{29}N_2O_4P$ |
| 43 | OMe | Me | H | H | 3-pyridyl | Et | 164–166 | $C_{18}H_{25}N_2O_5P$ |
| 44 | OMe | Me | H | H | 3-pyridyl | iPr | 123–125 | $C_{20}H_{29}N_2O_5P$ |
| 45 | OMe | nBu | H | H | 3-pyridyl | Et | 133–134 | $C_{21}H_{31}N_2O_5P$ |
| 46 | OMe | nBu | H | H | 3-pyridyl | iPr | 142–144 | $C_{23}H_{35}N_2O_5P$ |
| 47 | OMe | Me | H | H | 3-picolyl | Et | 99–101 | $C_{19}H_{27}N_2O_5P$ |
| 48 | OMe | Me | H | H | 3-picolyl | iPr | 85–86 | $C_{21}H_{31}N_2O_5P$ |
| 49 | OMe | Me | H | H | 4-picolyl | Et | 129–130 | $C_{19}H_{27}N_2O_5P$ |
| 50 | OMe | Me | H | H | 4-picolyl | iPr | 138–141 | $C_{21}H_{31}N_2O_5P$ |
| 51 | Me | Me | H | H | 3-pyridyl | iPr | 169–171 | $C_{20}H_{29}N_2O_4P$ |
| 52 | OEt | H | H | H | 3-pyridyl | iPr | 192–194 | $C_{20}H_{29}N_2O_5P$ |
| 53 | OEt | Me | H | H | 3-pyridyl | Et | 172–173 | $C_{19}H_{27}N_2O_5P$ |
| 54 | OEt | Me | H | H | 3-pyridyl | iPr | 177–178 | $C_{21}H_{31}N_2O_5P$ |
| 55 | OEt | OEt | H | H | 3-pyridyl | Et | 130–132 | $C_{20}H_{29}N_2O_6P$ |
| 56 | OEt | OEt | H | H | 3-pyridyl | iPr | 149–150 | $C_{22}H_{33}N_2O_6P$ |
| 57 | OMe | Et | H | H | 3-pyridyl | Et | 139–141 | $C_{19}H_{27}N_2O_5P$ |
| 58 | OMe | Et | H | H | 3-pyridyl | iPr | 146–148 | $C_{21}H_{31}N_2O_5P$ |
| 59 | OMe | OEt | H | H | 3-pyridyl | Et | 156–157 | $C_{19}H_{27}N_2O_6P$ |
| 60 | OMe | OEt | H | H | 3-pyridyl | iPr | 159–160 | $C_{21}H_{31}N_2O_6P$ |
| 61 | OMe | OMe | H | Me | 3-picolyl | Et | oil | *NMR and MS |
| 62 | OMe | OMe | H | Me | 3-picolyl | iPr | oil | *NMR and MS |
| 63 | OMe | Me | H | Me | 3-picolyl | Et | oil | *NMR and MS |
| 64 | OMe | Me | H | Me | 3-picolyl | iPr | oil | *NMR and MS |
| 65 | OMe | OMe | H | H | 3-pyridyl | Et | 153–157 | **$C_{18}H_{25}N_2O_6P$ |
| 66 | OMe | OMe | H | H | 3-pyridyl | Et | 155–158 | ***$C_{18}H_{25}N_2O_6P$ |
| 67 | OMe | OMe | H | H | phenyl | Et | 143–146 | $C_{19}H_{26}NO_6P$ |
| 68 | OMe | OMe | H | H | phenyl | iPr | 144–146 | $C_{21}H_{30}NO_6P$ |
| 69 | OMe | Me | H | H | 5-(2-methylpyridyl) | Et | 154–155 | $C_{19}H_{27}N_2O_5P$ |
| 70 | OMe | Me | H | H | 5-(2-methylpyridyl) | iPr | 149–150 | $C_{21}H_{31}N_2O_5P$ |
| 71 | OMe | Me | H | H | 3-(2-methylpyridyl) | Et | 150–152 | $C_{19}H_{27}N_2O_5P$ |
| 72 | OMe | Me | H | H | 3-(2-methylpyridyl) | iPr | 148–150 | $C_{21}H_{31}N_2O_5P$ |
| 73 | OMe | OMe | H | H | 3-(2-methylpyridyl) | Et | 146–148 | $C_{19}H_{27}N_2O_6P$ |

*Identified by NMR and MS spectroscopies
**(+) Enantiomer of Compound 20
***(−) Enantiomer of Compound 20

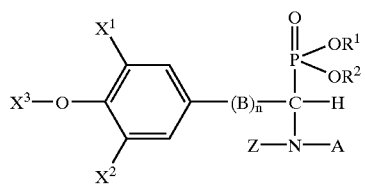

(I)

| Cpd | $X^1$ | $X^2$ | $X^3$ | $(B)_n$ | Z | R | mp (° C.) | Microanalysis |
|---|---|---|---|---|---|---|---|---|
| | H | | $OCH_2$ | bond | H | Et | 98–99 | $C_{17}H_{21}N_2O_5$ |
| | OMe | OMe | H | CH=CH | H | Et | foam | *NMR and MS |
| | OMe | OMe | H | $CH_2$—$CH_2$ | H | Et | 134–138 | $C_{20}H_{29}N_2O_6P$ |

*Identified by NMR and MS spectroscopies

Biological Data

In vitro Data—The compounds of formula (I) were tested for lowering the production of Lp(a) in primary cultures of Cynomolgus hepatocytes according to the assays described below. Two incubation times were used: 4 h for Assay 1 and 24 h for Assay 2.

Protocol—Hepatocytes were isolated from livers of adult Cynomolgus monkeys by the two-step collagenase perfusion method according to C. Guguen-Guillouzo and A. Guillouzo "Methods for preparation of adult and fetal hepatocytes" p.1–12 in "Isolated and Cultured Hepatocytes", les editions Inserm Paris and John Libbey Eurotext London (1986).

The viability of cells was determined by Trypan blue staining. The cells were then seeded at a density of $1.5$–$2.10^5$ viable cells per 2 $cm^2$ in 24 well tissue culture plates in a volume of 500 μl per well of Williams E tissue culture medium containing 10% fetal calf serum. Cells were incubated for 4–6 hours at 37° C. in a $CO_2$ incubator (5% $CO_2$) in the presence of 20 μM of the test compounds dissolved in ethanol. Four wells were used for each compound. Nicotinic acid and steroid hormones were used as references to validate the assay system since they are known to decrease Lp(a) in man. Control cells were incubated in the presence of ethanol only.

The amount of Lp(a) secreted in culture medium was directly assayed by ELISA using a commercially available kit. Cells were washed and lysed as described by A. L. White et al, Journal of Lipid Research vol 34, p. 509–517, (1993) and the cellular content of Lp(a) was assayed as described above.

Changes in Lp(a) concentration in culture medium are given as the percentage of value measured for the control plates at 4 h (Assay 1) or 24 h (Assay 2).

Results—Assay 1: compounds 2, 7, 11, 15, 16, 18 and 20 were found to change the concentrations of Lp(a) in the culture medium in the range from −12 to −34%.

Assay 2: compounds 1, 2, 3, 5, 7, 11, 13, 15, 17, 19, 20, 21, 26 to 29, 32, 34 to 52, 57 to 60, 65 and 66 were found to change the concentrations of Lp(a) in the culture medium in the range from −7 to −37%.

In Vivo Data—Study Protocol—Male cynomolgus monkeys weighing between 3 and 7 kg were divided into groups of 3 to 4 animals each. Prior to treatment their plasma Lp(a) levels were followed over a two month period to ascertain a constant baseline value. Test compounds were given orally by gavage at the dose of 25 mg/kg/day for 4 weeks and Lp(a) was measured at day 28. At the end of the dosing period, animals were maintained for a treatment free period of 4 weeks, whereupon their plasma Lp(a) levels returned to pretreatment levels. This control provided proof that the decrease in Lp(a) measured was caused by the pharmacological activity of the test compounds.

Results—At Days −7 and 28, after an overnight fast, blood samples were collected on EDTA and Lp(a) was measured by the highly sensitive and specific ELISA test. Results (mean of 3–4 values of each group) were expressed as % of predose (Day −7). Selected compounds of formula (I) were tested under the experimental conditions to investigate their pharmacological activity in vivo.

The compounds No 1, 2, 3, 7, 15, 17, 19, 20, 21, 27, 28, 32, 39, 44 and 52 lower plasma Lp(a) in the range of −13% to −51% (value measured at Day 28, % change from predose at Day −7).

The compounds of Formula (I) have therefore a therapeutic potential for the treatment of the following diseases where Lp(a) is associated with accelerated atherosclerosis, abnormal proliferation smooth muscle cells and increased thrombogenesis: coronary heart disease, peripheral artery disease: intermittent claudication, extracranial carotid atherosclerosis, stroke, restenosis after angioplasty and atherosclerosis occuring after heart transplant. The primary indications of these compounds would be the treatment of the diseases mentioned above.

What is claimed is:

1. A process for preparing a compound of formula (Ia):

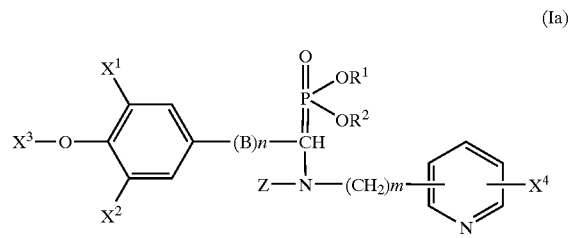

wherein $X^1$ is H, $C_{(1-3)}$alkyl, hydroxy or $C_{(1-4)}$alkoxy;

$X^2$ is $C_{(1-3)}$alkyl or $C_{(1-4)}$alkoxy;

$X^3$ is H or $C_{(1-4)}$alkyl;

$R^1$, $R^2$, which may be identical or different, are H or $C_{(1-3)}$alkyl;

B is $CH_2CH_2$, CH=CH, or $CH_2$;

n is zero or 1;

Z is H;

m is an integer from 1 to 5;

$X^4$ is H, or $C_{(1-8)}$alkyl, $C_{(1-8)}$alkoxy or halo;

and the pyridyl ring is attached by the ring carbon α- or β- to the nitrogen (2- or 3-pyridyl); which process comprises (a) treating an amine of formula (VII)

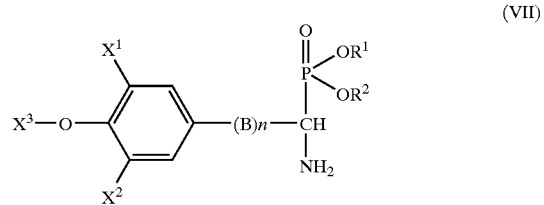

in which B, $R^1$, $R^2$, $X^1$, $X^2$, $X^3$ and n are as hereinbefore defined; with an aldehyde of formula (IX):

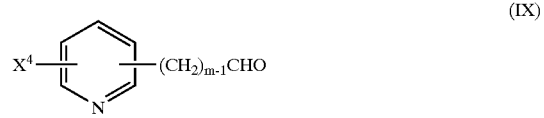

in which m and $X^4$ are as hereinbefore defined;

under reductive amination conditions.

2. A process for preparing an individual enantiomer of an aminophosphonate of formula (Ia) as defined in claim 1 which process comprises treating either of the (+) or (−) enantiomer of the α-substituted aminomethylphosphonate of formula (X):

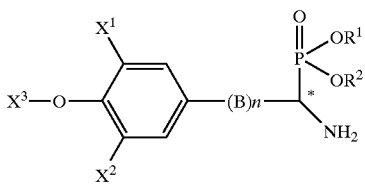

in which B, $R^1$, $R^2$, $X^1$, $X^2$, $X^3$ and n are as defined in claim 1;

with an aldehyde of formula (IX):

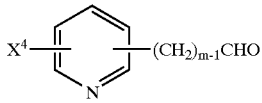

in which m and $X^4$ are as defined in claim 1;

under reductive amination conditions.

3. A process as claimed in claim 2 in which the reaction is carried out in the presence of sodium cyanoborohydride in an alcoholic solvent, preferably methanol, at a pH between 3 to 6 and at a temperature between 0° C. and 25° C.

4. A compound selected from the group consisting of:
diisopropyl α-(4-hydroxy-3-methoxy-5-methylphenyl)-N-(3-pyridyl)-aminomethylphosphonate;
dimethyl α-(3,5-dimethoxy-4-hydroxyphenyl)-N-(3-pyridyl)-aminomethylphosphonate;
diethyl α-(3,5-dimethoxy-4-hydroxyphenyl)-N-(3-pyridyl)-aminomethylphosphonate;
diisopropyl α-(3,5-dimethoxy-4-hydroxyphenyl)-N-(3-pyridyl)-aminomethylphosphonate;
diethyl α-(3,5-dimethyl-4-hydroxyphenyl)-N-(3-pyridyl)-aminomethylphosphonate; and
dimethyl α-(3-methyl-4-hydroxyphenyl-5-tert-butyl)-N-(3-pyridyl)-aminomethylphosphonate.

5. A pharmaceutical composition comprising a compound of claim 4 and a pharmaceutically acceptable carrier or excipient.

6. The compound of claim 4, wherein said compound is diisopropyl α-(4-hydroxy-3-methoxy-5-methylphenyl)-N-(3-pyridyl)-aminomethylphosphonate.

7. The compound of claim 6, wherein said compound is (+)diisopropyl α-(4-hydroxy-3-methoxy-5-methylphenyl)-N-(3-pyridyl)-aminomethylphosphonate.

8. The compound of claim 6, wherein said compound is (−)diisopropyl α-(4-hydroxy-3-methoxy-5-methylphenyl)-N-(3-pyridyl)-aminomethylphosphonate.

* * * * *